(12) United States Patent
Jakobsen et al.

(10) Patent No.: US 11,970,554 B2
(45) Date of Patent: Apr. 30, 2024

(54) LABELED OXYTOCIN AND METHOD OF MANUFACTURE AND USE

(71) Applicants: TONIX PHARMACEUTICALS HOLDING CORP., New York, NY (US); AARHUS UNIVERSITY, Aarhus (DK)

(72) Inventors: Steen Jakobsen, Risskov (DK); Michael Winterdahl, Risskov (DK); Erik Nguyen Nielsen, Aarhus (DK); David C. Yeomans, Sunnyvale, CA (US); Dean Carson, Palo Alto, CA (US)

(73) Assignees: TONIX PHARMACEUTICALS HOLDING CORP., New York, NY (US); AARHUS UNIVERSITY, Aarhus C (DK)

(*) Notice: Subject to any disclaimer, the term of this patent is extended or adjusted under 35 U.S.C. 154(b) by 57 days.

(21) Appl. No.: 16/976,912

(22) PCT Filed: Mar. 1, 2019

(86) PCT No.: PCT/US2019/020419
§ 371 (c)(1),
(2) Date: Aug. 31, 2020

(87) PCT Pub. No.: WO2019/169342
PCT Pub. Date: Sep. 6, 2019

(65) Prior Publication Data
US 2021/0002331 A1 Jan. 7, 2021

Related U.S. Application Data

(60) Provisional application No. 62/637,187, filed on Mar. 1, 2018.

(51) Int. Cl.
*C07K 7/16* (2006.01)
*A61K 51/08* (2006.01)
*G01N 33/60* (2006.01)

(52) U.S. Cl.
CPC .......... *C07K 7/16* (2013.01); *A61K 51/084* (2013.01); *G01N 33/60* (2013.01)

(58) Field of Classification Search
CPC ...... A61K 51/00; A61K 51/08; A61K 51/084; A61K 2123/00; A61K 2121/00; C07K 7/16; G01N 33/60
USPC ............ 424/1.11, 1.65, 1.69, 1.81, 9.1, 9.2; 530/300
See application file for complete search history.

(56) References Cited

U.S. PATENT DOCUMENTS

| 1,936,364 A | 11/1933 | Pasternack et al. |
| 2,260,004 A | 10/1941 | Devenport et al. |
| 2,938,891 A | 5/1960 | Velluz et al. |
| 3,076,797 A | 2/1963 | Velluz et al. |
| 5,988,449 A | 11/1999 | Fuchs et al. |
| 7,784,460 B2 | 10/2010 | Djupesland et al. |
| 7,854,227 B2 | 12/2010 | Djupesland et al. |
| 9,629,894 B2 * | 4/2017 | Yeomans ............... A61K 45/06 |
| 2010/0311655 A1 | 12/2010 | Leonard et al. |
| 2016/0193282 A1 | 7/2016 | Yeomans |

FOREIGN PATENT DOCUMENTS

| JP | 2004161664 A | 6/2004 |
| JP | 201085108 A | 4/2010 |
| JP | 2016114573 A | 6/2016 |
| WO | WO2004062563 | 7/2004 |
| WO | 2005084715 A2 | 9/2005 |
| WO | 2006036071 A2 | 4/2006 |
| WO | 2010116209 A1 | 10/2010 |
| WO | 2011106732 A1 | 9/2011 |
| WO | WO2012042371 | 4/2012 |
| WO | 2017096036 A1 | 6/2017 |

OTHER PUBLICATIONS

Miller et al (Angew. Chem. Int. Ed, vol. 47, pp. 8998-9033). (Year: 2008).*
Blower et al, EJNMMI Radiopharmacy and Chemistry, vol. 2, No. 16, 10 pages (Year: 2017).*
Saji et al, Nucl. Med. Biol., vol. 19, No. 4, pp. 455-460. (Year: 1992).*
Live et al, Journal of the American Chemical Society, vol. 101, No. 2, pp. 474-479 (Year: 1979).*
Atke et al., "Uterotonic activity and myometrial receptor affinity of 1-deamino-1-carba-2-tyrosine(O-methyl)-oxytocin," Acta Endocrinologica, 115(1):155-160 (1987).
Engstrom et al., "Oxytocin receptor binding and uterotonic activity of carbetocin and its metabolites following enzymatic degradation," European Journal of Pharmacology, 355(2-3):203-210 (1998).
Kim et al., "The Prevalence of Anxiety and Mood Problems among Children with Autism and Asperger Syndrome," Autism, 4(2):117-132 (2000).
Miller et al., "Synthesis of 11C, 18F, 15O, and 13N radiolabels for positron emission tomography," Angewandte Chemie International Edition, 47(47):8998-9033 (2008).
Smith et al., "Synthesis and evaluation of C-11, F-18 and I-125 small molecule radioligands for detecting oxytocin receptors," Bioorganic & Medicinal Chemistry, 20(8):2721-2738 (2012).

(Continued)

*Primary Examiner* — D. L. Jones
(74) *Attorney, Agent, or Firm* — HALEY GUILIANO LLP; James F. Haley, Jr.; Mihaela D. Danca

(57) ABSTRACT

Disclosed are $^{13}$N-oxytocin molecules, methods of manufacture of $^{13}$N-oxytocin molecules and methods of use of $^{13}$N-oxytocin molecules in the determination of the distribution and kinetics of $^{13}$N-oxytocin molecules after craniofacial or other application methods.

5 Claims, 3 Drawing Sheets

Specification includes a Sequence Listing.

(56) References Cited

OTHER PUBLICATIONS

Staszczuk et al., "Methods of Preparation of Magnesium Organic Compounds from Natural Dolomite," Physicochem Problems of Mineral Processing, 37:149-158 (2003).
Vavere et al., "Molecular Imaging of Cancer with Radiolabeled Peptides and PET," Anticaner Agents in Medicinal Chemistry, 12(5):462-475 (2012).
Veinante et al., "Distribution of oxytocin- and vasopressin-binding sites in the rat extended amygdala: a histoautoradiographic study," Journal of Comparative Neurology, 383(3):305-325 (1997).
Wenzel et al., "Development of a Novel Nonpeptidic 18 F-Labeled Radiotracer for in Vivo Imaging of Oxytocin Receptors with Positron Emission Tomography," Journal of Medicinal Chemistry, 59(5):1800-1817 (2016).
Wisniewki et al., "New, potent, and selective peptidic oxytocin receptor agonists," Journal of Medicinal Chemistry, 57(12):5306-5317 (2014).
Budesinsky et al., "Synthesis and utilization of 13C and 15N backbone-labeled proline: NMR study of synthesized oxytocin with backbone-labeled C-terminal tripeptide amide," Amino Acids, 29(2):151-160 (2005).
Kheterpal et al., "Mass spectrometric quantification of MIF-1 in mouse brain by multiple reaction monitoring," Peptides, 30(7):1276-1281 (2009).
Kiso et al., "A synthetic method suitable for the rapid preparation of 13N-labeled dermorphin analogue, H-Tyr-D-Met (O)-Phe-Gly-NH2 (SD-62)," Chemical and Pharmaceutical Bulletin, 39(10):2734-2736 (1991).
Saji et al., "Synthesis and biological evaluation of a 13N-labeled opioid peptide," Nuclear Medicine and Biology, 19(4):455-460 (1992).
Jelinski et al., "C-Terminal 18F-fluoroethylamidation exemplified on [Gly-OH9] oxytocin," Journal of Labelled Compounds and Radiopharmaceuticals, 45:217-229 (2002).

* cited by examiner

LABELED OXYTOCIN AND METHOD OF MANUFACTURE AND USE

CROSS-REFERENCE TO RELATED APPLICATIONS

This application is a United States National Phase Application filed under 35 U.S.C. § 371 of International Patent Application No. PCT/US2019/020419, filed on Mar. 1, 2019, which claims the benefit of and priority from U.S. Provisional Application 62/637,187, filed Mar. 1, 2018, the contents of each of which are incorporated by reference herein in their entirety.

SUBMISSION OF SEQUENCE LISTING ON ASCII TEXT FILE

This instant application contains a Sequence Listing which has been submitted electronically in ASCII format and is hereby incorporated herein by reference in its entirety. Said ASCII copy, created on Aug. 21, 2020, is named 104545-0068-301-SL and is 1,276 bytes in size.

FIELD OF THE INVENTION

The invention relates to a $^{13}$N-radiolabeled oxytocin peptide for use in Positron Emission Tomography (PET) and other uses, including compositions comprising the $^{13}$N-radiolabeled oxytocin peptide and methods of manufacturing the $^{13}$N-radiolabeled oxytocin peptide.

BACKGROUND

Oxytocin is a naturally occurring 9 amino acid polypeptide that has been implicated in multiple physiologic body functions, including uterine contraction, muscle regeneration, and lactation. In addition, oxytocin has been demonstrated to play an important role in several peripheral and central nervous system functions. For example, oxytocin has been shown to be involved in pain, autism, appetite, anxiety, trust, control of blood sugar, and interpersonal connection.

Published accounts have demonstrated that craniofacial mucosal, e.g., nasal, administration of oxytocin has been shown to have the capacity to modulate these functions. For example, nasal oxytocin administration has been shown to improve social function in autistic patients, and to attenuate pain in migraine headache patients. However, no information is available describing the spatio-temporal distribution of oxytocin within the body following craniofacial mucosal application. Unlike measurements of blood levels of oxytocin, it is inherently difficult to measure levels of oxytocin in tissue, and particularly the nervous system, following application of oxytocin. The ability to assess tissue levels of oxytocin after craniofacial or other application would allow determination of tissue oxytocin levels that are critical for treatment efficacy.

One approach for evaluating the biodistribution of administered oxytocin is through positron emission tomography (PET). PET is a nuclear medical imaging technique that produces an image or picture of functional processes in a body. The system detects pairs of gamma rays emitted indirectly by a positron-emitting radionuclide (tracer, radiotracer, radiopharmaceutical, etc.), which is introduced into the body on a biologically active molecule. A radionuclide, or a radioactive nuclide, is an atom with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles. These emissions constitute ionizing radiation. Radionuclides are often referred to as radioactive isotopes or radioisotopes. Three-dimensional distribution of radionuclide concentration within the body may be constructed by computer analysis in the PET process. However, the synthesis of radiolabeled oxytocin peptides for use as radiotracers in PET remains challenging.

The disclosures of all publications, patents, patent applications and published patent applications referred to herein are hereby incorporated herein by reference in their entirety.

BRIEF SUMMARY OF THE INVENTION

The present application provides $^{13}$N-Oxytocin, compositions comprising $^{13}$N-Oxytocin, methods of using $^{13}$N-Oxytocin, and methods of manufacturing $^{13}$N-Oxytocin.

In some embodiments, there is provided an $^{13}$N-labeled oxytocin peptide comprising the amino acid sequence of SEQ ID NO: 1. In some embodiments, one component $^{14}$N atom of the oxytocin peptide is replaced by an $^{13}$N radionuclide. In some embodiments, one residue of the oxytocin peptide is modified to comprise a moiety comprising an $^{13}$N radionuclide. In some embodiments, one residue of the oxytocin peptide is modified to comprise $^{13}$NH$_2$. In some embodiments, the $^{13}$N-labeled oxytocin peptide comprises a single $^{13}$N radionuclide.

In some embodiments, according to any of the $^{13}$N-labeled oxytocin peptides described above, the $^{13}$N-labeled oxytocin peptide comprises an $^{13}$N radionuclide at a) the glutamine residue at position 4 (SEQ ID NO: 2); b) the asparagine residue at position 5 (SEQ ID NO: 3); or c) the glycine residue at position 9 (SEQ ID NO: 4).

In some embodiments, the $^{13}$N-labeled oxytocin peptide is the compound of Formula (IV).

In some embodiments, there is provided a method of manufacturing an $^{13}$N-labeled oxytocin peptide comprising the amino acid sequence of SEQ ID NO: 1, the method comprising: a) reacting the compound of Formula (Ib) with diethyl cyanophosphonate (DECP) to provide the compound of Formula (IIb); b) reacting the compound of Formula (IIb) with gaseous $^{13}$NH$_3$ to provide the compound of Formula (IIIb); and c) deprotecting the compound of Formula (IIIb) to provide the $^{13}$N-labeled oxytocin peptide, wherein the $^{13}$N-labeled oxytocin peptide is the compound of Formula (IV). In some embodiments, reacting the compound of Formula (Ib) with DECP is carried out in the presence of dimethyl sulfoxide (DMSO), tetrahydrofuran (THF), and pentamethylpiperidine (PMP). In some embodiments, the amount of DECP is between about 0.7 and about 1.1 equivalents. In some embodiments, the ratio of DMSO to THF is between about 1:7 and about 1:11. In some embodiments, the deprotecting comprises reacting the compound of Formula (IIIb) with HCl/dioxane.

In some embodiments, according to any of the methods described above, the method further comprises purifying the $^{13}$N-labeled oxytocin peptide provided in step c) to remove reagents, organic solvents, and precursor. In some embodiments, the purifying comprises purification by solid-phase extraction (SPE). In some embodiments, purification by SPE comprises: a) applying the $^{13}$N-labeled oxytocin peptide to a first hydrophobic SPE column, such that the $^{13}$N-oxytocin and precursor are retained on the first hydrophobic SPE column; b) applying a solution comprising an aqueous ion-pairing reagent to the first hydrophobic SPE column, such that the $^{13}$N-oxytocin is eluted in a first eluate; c) applying the first eluate to a second hydrophobic SPE column, such that the $^{13}$N-oxytocin of the first eluate is retained on the second hydrophobic SPE column; and d) eluting the $^{13}$N-oxytocin in a second eluate. In some embodiments, the first and/or second hydrophobic SPE columns comprise a silica-based bonded phase with strong hydrophobicity. In some embodiments, the solution comprising an aqueous ion-pairing reagent comprises between about 15% and about 25% acetonitrile.

In some embodiments, there is provided an $^{13}$N-labeled oxytocin peptide prepared by a process comprising a method according to any of the methods described above.

In some embodiments, there is provided a method of determining the distribution of exogenously administered oxytocin in an individual, comprising: a) administering to the individual an $^{13}$N-labeled oxytocin peptide according to any of the $^{13}$N-labeled oxytocin peptides described above; b) allowing the $^{13}$N-labeled oxytocin peptide to accumulate at a tissue or cell site to be imaged; and c) imaging the cells or tissues with a non-invasive imaging technique.

In some embodiments, there is provided a method of determining the distribution of oxytocin receptors in an individual, comprising: a) administering to the individual an $^{13}$N-labeled oxytocin peptide according to any of the $^{13}$N-labeled oxytocin peptides described above; b) allowing the $^{13}$N-labeled oxytocin peptide to bind to oxytocin receptors; and c) imaging the $^{13}$N-labeled oxytocin peptide in the individual with a non-invasive imaging technique.

In some embodiments, there is provided a method of determining the kinetics of exogenously administered oxytocin in an individual, comprising: a) administering to the individual an $^{13}$N-labeled oxytocin peptide according to any of the $^{13}$N-labeled oxytocin peptides described above; and b) imaging the $^{13}$N-labeled oxytocin peptide in the individual over a period of time with a non-invasive imaging technique.

In some embodiments, according to any of the methods described above, the non-invasive imaging technique comprises positron emission tomography imaging. In some embodiments, the non-invasive imaging technique comprises positron emission tomography with computed tomography imaging or positron emission tomography with magnetic resonance imaging.

In some embodiments, according to any of the methods described above, the $^{13}$N-labeled oxytocin peptide is administered via craniofacial mucosal administration. In some embodiments, the $^{13}$N-labeled oxytocin peptide is administered intranasally.

In some embodiments, according to any of the methods described above, the $^{13}$N-labeled oxytocin peptide is administered intravenously, intraarterially, intraperitoneally, intravesicularly, subcutaneously, intrathecally, intrapulmonarily, intramuscularly, intratracheally, ocularly, transdermally, or by suppository. In some embodiments, the $^{13}$N-labeled oxytocin peptide is administered intravenously.

In some embodiments, there is provided a kit comprising an $^{13}$N-labeled oxytocin peptide according to any of the $^{13}$N-labeled oxytocin peptides described above.

DETAILED DESCRIPTION OF THE INVENTION

Figure 1:
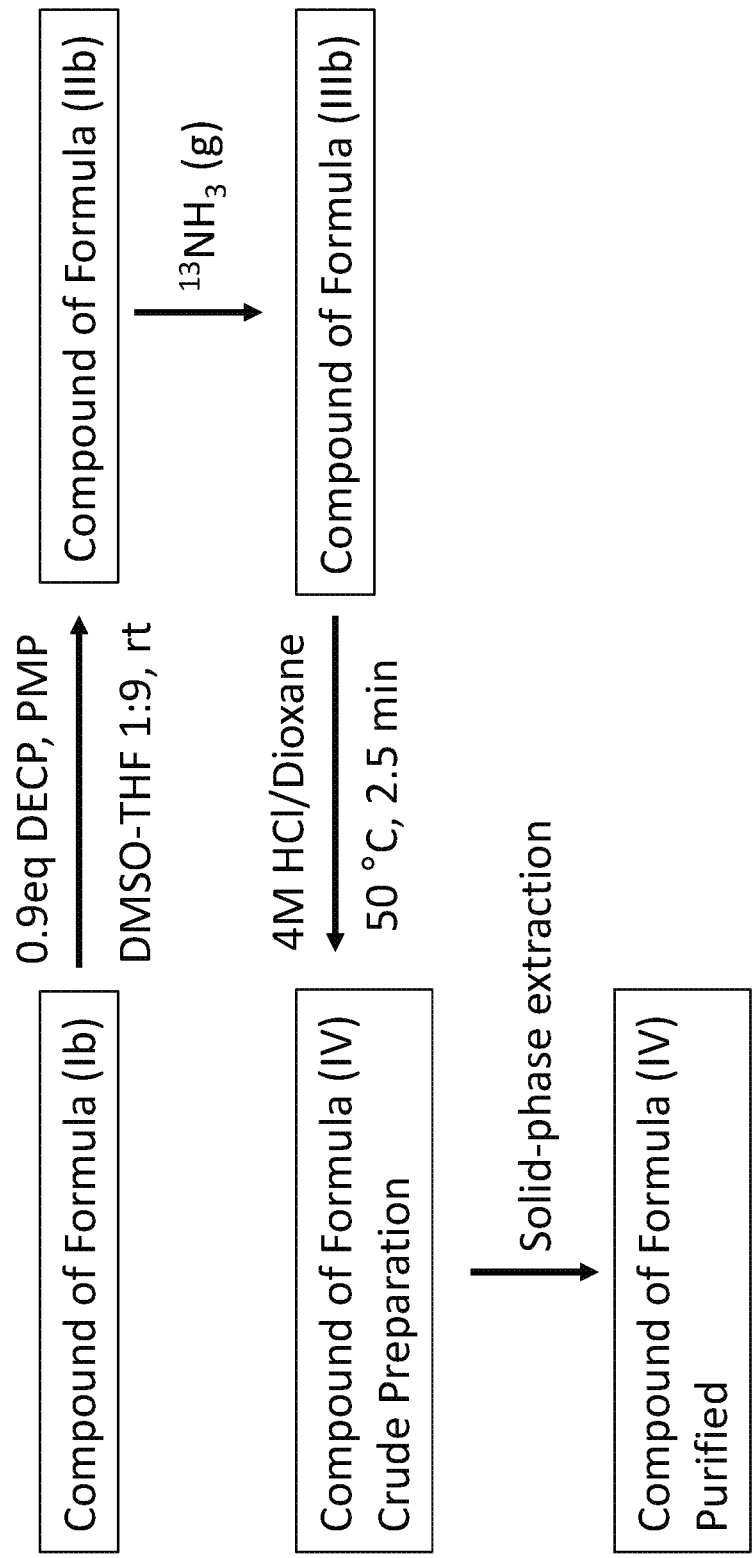
FIG. 1 shows a flow chart for the synthesis and manufacture of $^{13}$N-oxytocin.

In order for oxytocin to be therapeutically effective for a particular indication, it must be efficiently delivered to the appropriate target tissue. Delivery can be affected by parameters including route of application and formulation composition. Being able to precisely determine the spatial and temporal distribution of oxytocin administered by routes and formulations shown to be effective for treating particular indications will allow for determining therapeutically effective pharmacokinetic profiles for said indications. Knowledge of these pharmacokinetic profiles will allow for evaluating new combinations of administration route and formulation to maximize therapeutic efficacy. Furthermore, uncovering the sites of action of oxytocin for treating various indications may provide additional therapeutic targets for investigation.

The synthesis of radiolabeled oxytocin peptides has remained a challenge, presenting an obstacle to the use of conventional imaging technologies such as PET. Provided herein are novel $^{13}$N-labeled oxytocin peptides and methods of their manufacture.

Definitions

As used herein, "oxytocin peptide" refers to a substance having biological activity associated with natural oxytocin. Oxytocin peptide can be a naturally occurring endogenous peptide, fragments, analogues or derivatives thereof. Oxytocin peptide can also be a non-endogenous peptide, fragments, analogues or derivatives thereof. In one aspect, the oxytocin peptide is human oxytocin. In other aspects, the oxytocin peptide may be an analogue or derivative of human oxytocin.

As used herein, an "analogue" or "derivative" refers to any peptide analogous to naturally occurring oxytocin wherein one or more amino acids within the peptide have been substituted, deleted, or inserted. The term also refers to any peptide wherein one or more amino acids (for example one, two or three amino acids) have been modified, for example by chemical modification. In general, the term covers all peptides which exhibit oxytocin activity but which may, if desired, have a different potency or pharmacological profile.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating" refers to an approach for obtaining beneficial or desired results including but not limited to a therapeutic benefit. By therapeutic benefit is meant any therapeutically relevant improvement in or effect on one or more diseases, conditions, or symptoms under treatment.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

"Craniofacial mucosal administration" refers to delivery to the mucosal surfaces of the nose, nasal passageways, nasal cavity; the mucosal surfaces of the oral cavity including the gingiva (gums), the floor of the oral cavity, the lips, the tongue, the sublingual oral surfaces, including the frenulum of tongue and the floor of the mouth, and the mucosal surfaces of or around the eye including the conjunctiva, the lacrimal gland, the nasolacrimal ducts, and the mucosa of the upper or lower eyelid and the eye.

"Intranasal administration" or "administered intranasally" refers to delivery to the nose, nasal passageways or nasal cavity by spray, drops, powder, gel, film, inhalant or other means.

The "inferior region of the nasal cavity" refers generally to the portion of the nasal cavity where the middle and inferior turbinate bones protrude and is a region of the nasal cavity that is significantly innervated by the trigeminal nerve. The "superior region of the nasal cavity" is defined by the upper third and cribriform plate region wherein olfactory innervation is located.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein, the singular form "a", "an", and "the" includes plural references unless indicated otherwise.

Reference to "about" a value or parameter herein includes (and describes) embodiments that are directed to that value or parameter per se. For example, description referring to "about X" includes description of "X."

Where a range of values is provided, it is intended that each intervening value between the upper and lower limit of that range and any other stated or intervening value in that stated range is encompassed within the disclosure. For example, if a range of 1 µg to 8 µg is stated, it is intended that 2 µg, 3 µg, 4 µg, 5 µg, 6 µg, and 7 µg are also explicitly disclosed, as well as the range of values greater than or equal to 1 µg and the range of values less than or equal to 8 µg. If a range of 10-14% is stated, it is intended that 10%, 11%, 12%, 13%, and 14% are also explicitly disclosed. Furthermore, each smaller range in a stated range between any stated value or intervening value and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

The compositions and methods of the present invention may comprise, consist of, or consist essentially of the essential elements and limitations of the invention described herein, as well as any additional or optional ingredients, components, or limitations described herein or otherwise useful.

Unless otherwise noted, technical terms are used according to conventional usage.

$^{13}$N-Oxytocin

Oxytocin was one of the first peptide hormones to be isolated and sequenced.

Natural oxytocin is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO: 1).

There are processes described for the production of oxytocin, see for example U.S. Pat. Nos. 2,938,891 and 3,076,797; in addition, oxytocin is commercially available. A variety of peptide analogues and derivatives are available and others can be contemplated for use within the invention and can be produced and tested for biological activity according to known methods. Oxytocin analogues may include, but are not limited to, 4-threonine-1-hydroxy-deaminooxytocin, 4-serine-8-isoleucine-oxytocin, 9-deamidooxytocin, 7-D-proline-oxytocin and its deamino analogue, (2,4-diisoleucine)-oxytocin, deamino oxytocin analogue, 1-deamino-1-monocarba-E12-Tyr(OMe)]-OT(dCOMOT), 4-threonine-7-glycine-oxytocin (TG-OT), oxypressin, deamino-6-carba-oxytoxin (dC60), L-371,257 and the related series of compounds containing an ortho-trigluoro-ethoxyphenylacetyl core such as L-374,943. Other exemplary oxytocin analogues include 4-threonine-1-hydroxy-deaminooxytocin, 9-deamidooxytocin, an analogue of oxytocin containing a glycine residue in place of the glycinamide residue, 7-D-proline-oxytocin (2,4-diisoleucine)-oxytocin, an analogue of oxytocin with natriuretic and diuretic activities, deamino oxytocin analogue; a long-acting oxytocin analogue, 1-deamino-1-monocarba-E12-[Tyr(OMe)]-OT(dCOMOT), carbetocin, (1-butanoic acid-2-(O-methyl-L-tyrosine)-1-carbaoxytocin, deamino-1 monocarba-(2-O-methyltyrosine)-oxytocin [d(COMOT)]), [Thr4-Gly7]-oxytocin (TG-OT), oxypressin, Ile-conopressin, deamino-6-carba-oxytoxin (dC60), d[Lys(8)(5/6C-Fluorescein)]VT, d[Thr(4), Lys(8)(5/6C-Fluorescein)]VT, [HO(1)][Lys(8)(5/6C-Fluorescein)]VT, [HO(1)][Thr(4), Lys(8)(5/6CFluorescein)]VT, d[Orn(8)(5/6C-Fluorescein)]VT, d[Thr(4), Orn(8)(5/6C-Fluorescein)]VT, [HO(1)][Orn(8)(5/6C-Fluorescein)]VT, [HO(1)][Thr(4), Orn(8)(5/6C-Fluorescein)]VT, and 1-deamino-oxytocin in which the disulfide bridge between residues 1 or 6 is replaced by a thioether, and desamino-oxytocin analogues in which the disulfide bond is replaced by a diselenide bond, a ditelluride bond, a telluroseleno bond, a tellurosulfide bond or a selenosulfide bond (e.g., the peptide analogues of oxytocin described in PCT patent application WO 2011/120,071, incorporated herein by reference). Peptides for use within the invention can be peptides that are obtainable by partial substitution, addition, or deletion of amino acids within a naturally occurring or native peptide sequence. Peptides can be chemically modified, for example, by amidation of the carboxyl terminus (—$NH_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain the desired biological activity of the native oxytocin peptide. In some embodiments, the oxytocin analogue is 4-serine-8-isoleucine-oxytocin or 9-deamidooxytocin. In some embodiments, the oxytocin analogue is carbetocin. The present disclosure also embrace other known oxytocin analogs, for example, the peptidic oxytocin receptor agonists described in PCT patent application WO 2012/042371 and Wisniewski, et al. *J Med Chem.* 2014, 57:5306-5317, the entire content of which is incorporated herein by reference. In some embodiments, the oxytocin analogue is a compound selected from Compound Nos. 1-65 described in Tables 1-3 in Wiśniewski, et al. *J Med Chem.* 2014, 57:5306-5317. In some embodiments, the oxytocin analogue is a selected from the group consisting of Compound No. 31 ([2-ThiMeGly7]dOT), Compound No. 47 (carba-6-[Phe2,BuGly7]dOT), Compound No. 55 (carba-6-[3-MeBzlGly7]dOT) and Compound No. 57 (carba-1-[4-FBzlGly7]dOT, also referred to as merotocin).

An "international unit" (IU, UI or IE) is an internationally accepted unit of activity used to quantify vitamins, hormones and vaccines. It defines the amount of a substance that gives a unit of activity as determined using a defined biological assay in order to standardize preparations from multiple source materials. Similarly, a USP unit is a defined dosage unit established by the United States Pharmacopeia in cooperation with the Food and Drug Administration in order to ensure the identity, strength, quality, purity and consistency of a drug product. In general, USP units are equal to International Units, due to harmonization efforts. By convention, for oxytocin, 1 unit of activity is generally defined as equal to approximately 2 micrograms of synthetic oxytocin peptide; or 1 mg is equal to 500 units (Stedman's Medical Dictionary). Therefore, as used herein, one "IU" or "International Unit" of an oxytocin peptide is the amount of the oxytocin peptide that has the same biological activity or produces the same level of a biological effect (e.g. contractile response of rat uterine strips) as approximately 2 micrograms of the synthetic peptide. An analogue with weaker activity would require more material to achieve the same level of biological effect. Determinations of drug potency are well known to those skilled in the art and may include either in vitro or in vivo assays using synthetic oxytocin as a reference. Atke and Vilhardt *Acta Endocrinol* 1987: 115 (1):155-60; Engstrom et al. *Eur J Pharmacol* 1998: 355(2-3):203-10.

In some embodiments, the invention provides $^{13}N$-labeled oxytocin (also referred to herein as "$^{13}N$-oxytocin"). In some embodiments, at least one component $^{14}N$ atom of the oxytocin peptide is replaced by an $^{13}N$ radionuclide. In some embodiments, at least one amino acid of the oxytocin peptide is modified to comprise a moiety comprising an $^{13}N$ radionuclide. In some embodiments, the moiety comprising an $^{13}N$ radionuclide is $^{13}NH_2$. In some embodiments, the $^{13}N$-oxytocin peptide comprises a single $^{13}N$ radionuclide. In some embodiments, the $^{13}N$-oxytocin peptide comprises a single $^{13}N$ radionuclide in the glutamine residue at position 4. In some embodiments, the $^{13}N$-oxytocin peptide comprises a single $^{13}N$ radionuclide in the asparagine residue at position 5. In some embodiments, the $^{13}N$-oxytocin peptide comprises a single $^{13}N$ radionuclide in the glycine residue at position 9. In some embodiments, the $^{13}N$-oxytocin peptide comprises a glutamine, asparagine, or glycine residue modified to comprise $^{13}NH_2$. In some embodiments, the $^{13}N$-oxytocin peptide is the compound of Formula (IV). In some embodiments, the $^{13}N$-oxytocin peptide is prepared by a process comprising a method of preparing an $^{13}N$-oxytocin peptide according to any of the embodiments described herein.

Methods of Preparation

In some embodiments, there is provided a method of preparing an $^{13}N$-oxytocin peptide. The $^{13}N$-oxytocin peptides of the invention may be prepared by a number of processes as generally described below and more specifically in the Examples hereinafter. In the following process descriptions, the symbols when used in the formulae depicted are to be understood to represent those groups described in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography (e.g., HPLC), recrystallization, and other conventional separation procedures may also be used with intermediates or final products where it is desired to obtain a particular isomer of a compound or to otherwise purify a product of a reaction.

The compound of formula (IV) can be prepared according to Scheme 1, wherein PG1 is an amine protecting group (e.g., tert-butyloxycarbonyl (Boc), 9-fluorenylmethyloxycarbonyl (Fmoc), 2,2,2-trichloroethyl formyl (Troc), carboxybenzyl, and allyloxycarbonyl), R is phosphonate (e.g., diethyl phosphonate), $C_1$-$C_6$ alkyl (e.g, ethyl), benzyl, silyl (e.g., trimethylsilyl), or acyl (e.g., acetyl), and LG is a leaving group (e.g., OH, O-acyl, OAt, OBt, Cl, 1-imidazolyl, and the like).

Scheme 1
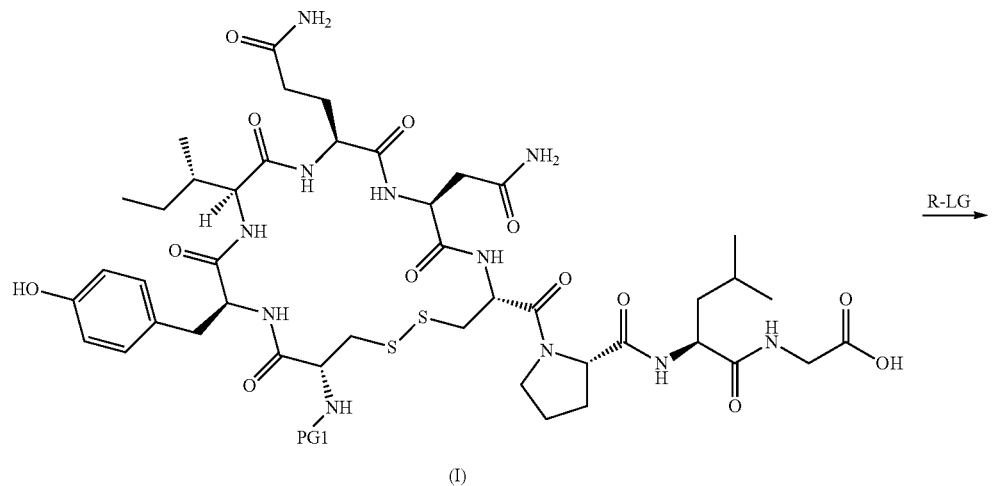
(I)
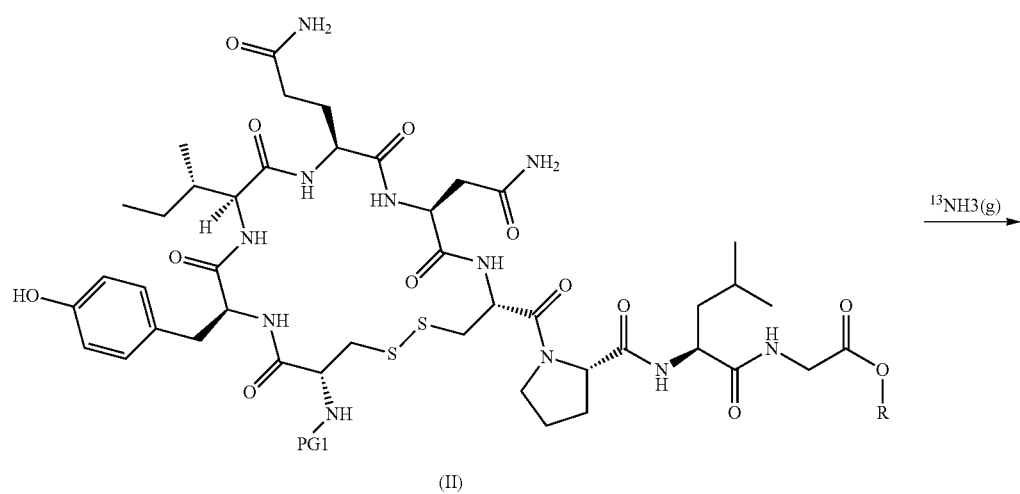
(II)
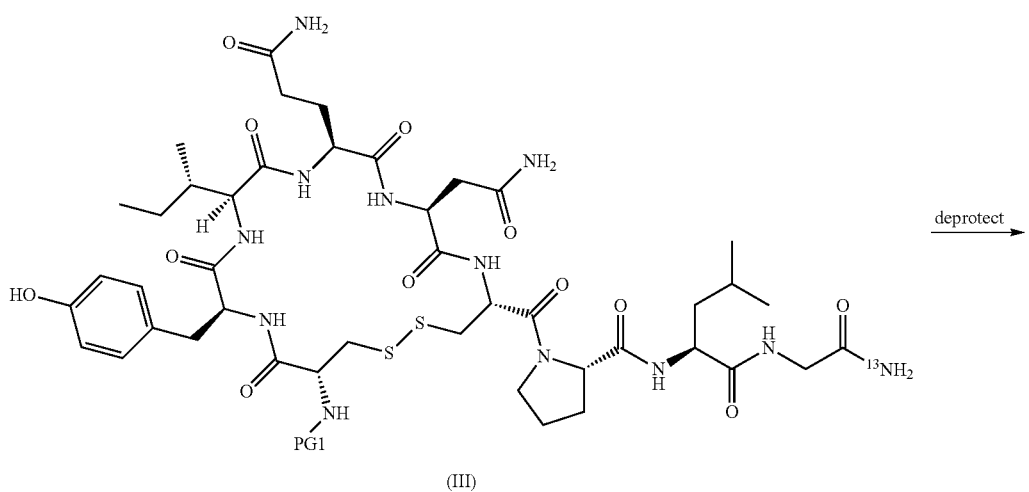
(III)

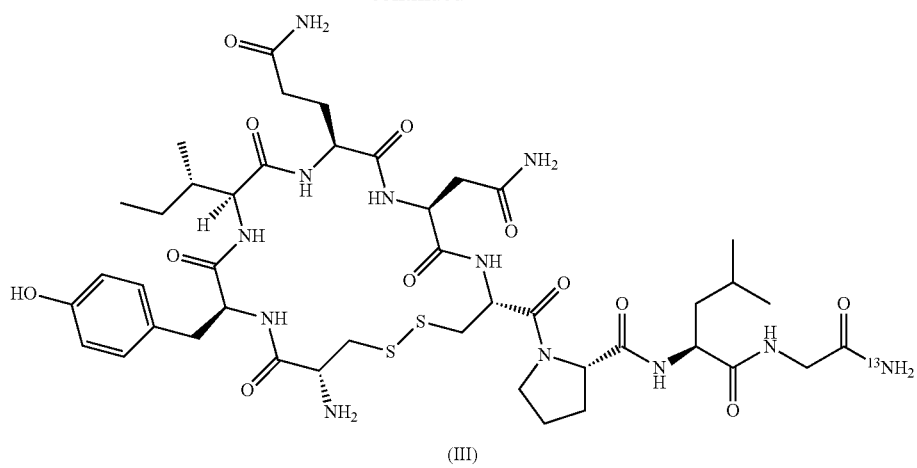 [SMILES: CC[C@H](C)[C@@H]1NC(=O)[C@H](Cc2ccc(O)cc2)NC(=O)[C@@H](N)CSSC[C@@H](C(=O)N2CCC[C@H]2C(=O)N[C@@H](CC(C)C)C(=O)NCC([13NH2])=O)NC(=O)[C@H](CC(N)=O)NC(=O)[C@H](CCC(N)=O)NC1=O ; "(IV)"]

(III)

Coupling of compound (I) with R-LG provides intermediate compound (II). In some embodiments, R-LG is diethyl cyanophosphonate (DECP). In some embodiments, coupling of compound (I) with R-LG is carried out in situ in a reaction vessel. Compound (II) is converted to compound (III) in the presence of gaseous $^{13}NH_3$. In some embodiments, the gaseous $^{13}NH_3$ is produced by proton irradiation of a liquid target (e.g., [$^{16}O$ (p, α)$^{13}N$]) to form aqueous $^{13}NH_3$, followed by combining the aqueous $^{13}NH_3$ with neat alkali hydroxide (e.g., NaOH) to release gaseous $^{13}NH_3$. In some embodiments, the liquid target is [$^{16}O$ (p, α)$^{13}N$]. In some embodiments, the neat alkali hydroxide is NaOH. In some embodiments, the aqueous $^{13}N_3$-solution is transferred to a vessel containing the neat alkali hydroxide (e.g., NaOH) to release gaseous $^{13}NH_3$, such as through Teflon tubing with helium flow. In some embodiments, compound (II) is converted to compound (III) in the presence of gaseous $^{13}NH_3$ at a temperature between about 0° C. and about 65° C. (such as about any of 0, 5, 10, 20, 30, 40, 50, 60, or 65° C., including any ranges between these values). In some embodiments, the released gaseous $^{13}NH_3$ is transferred to the reaction vessel containing compound (II). In some embodiments, the released gaseous $^{13}NH_3$ is transferred to the reaction vessel containing compound (II) manually by positive pressure, such as by using a syringe. Deprotection of the amine of compound (III) provides the compound of formula (IV).

It is understood that where protection of certain active or incompatible groups (e.g., an amine or a carboxylic acid) is required, the formulae in Scheme 1 intend and include compounds where such active or incompatible groups are in appropriate protected forms. For a general description of protecting groups and their use, see P. G. M. Wuts and T. W. Greene, Greene's Protective Groups in Organic Synthesis 4$^{th}$ edition, Wiley-Interscience, New York, 2006. A preparative embodiment of the preparative method in Scheme 1 is shown in Scheme 1a, wherein $R^1$ and $R^2$ are independently $C_1$-$C_6$ alkyl or $C_6$-$C_{14}$ aryl, wherein the $C_1$-$C_6$ alkyl and $C_6$-$C_{14}$ aryl of $R^1$ and $R^2$ are independently optionally substituted by halogen, cyano or $C_1$-$C_6$ alkyl, PG1 is an amine protecting group (e.g., tert-butyloxycarbonyl (Boc), 9-fluorenylmethyloxycarbonyl (Fmoc), 2,2,2-trichloroethyl formyl (Troc), carboxybenzyl, and allyloxycarbonyl), and LG is a leaving group (e.g., OH, O-acyl, OAt, OBt, Cl, 1-imidazolyl, and the like).

Scheme 1a

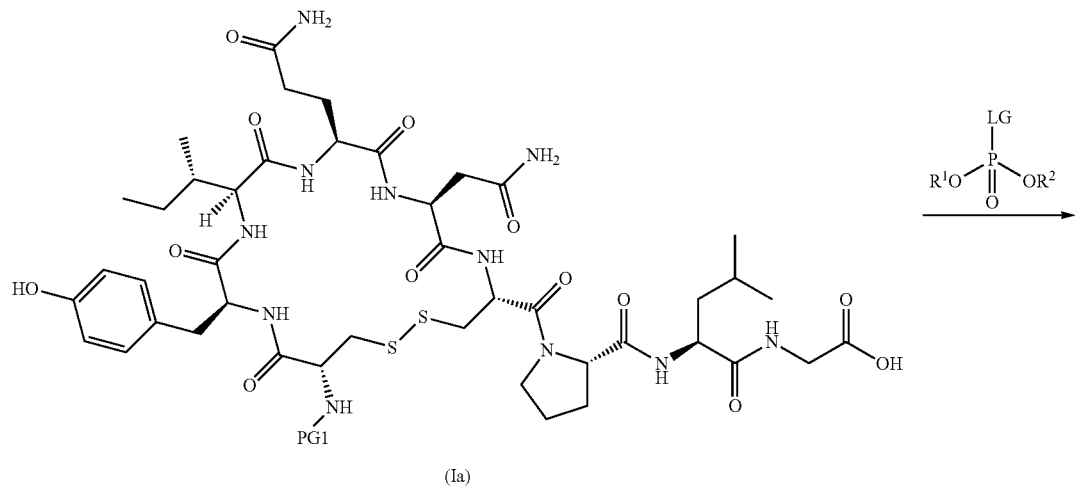

(Ia)

-continued

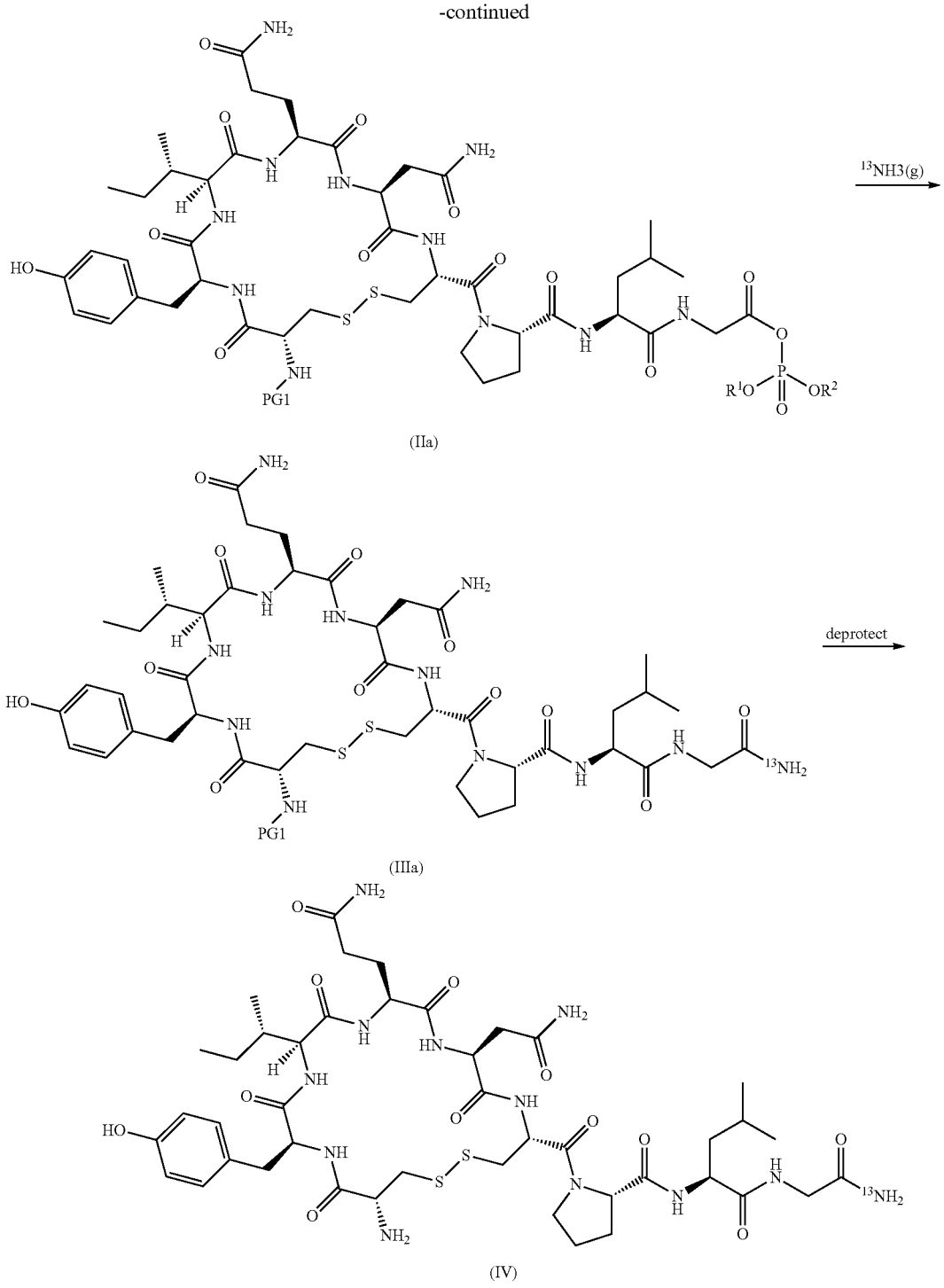

Coupling of compound (Ia) with phosphonate compound LG-P(=O)(OR¹)(OR²) (e.g., diethyl cyanophosphonate) provides intermediate compound (IIa). In some embodiments, coupling of compound (Ia) with LG-P(=O)(OR¹)(OR²) is carried out in situ in a reaction vessel. Compound (IIa) is converted to compound (IIIa) in the presence of gaseous $^{13}NH_3$. In some embodiments, the gaseous $^{13}NH_3$ is produced by proton irradiation of a liquid target (e.g., [$^{16}O$ (p, α)$^{13}N$]) to form aqueous $^{13}NH_3$, followed by combining the aqueous $^{13}NH_3$ with neat alkali hydroxide (e.g., NaOH) to release gaseous $^{13}NH_3$. In some embodiments, the liquid target is [$^{16}O$ (p, α)$^{13}N$]. In some embodiments, the neat alkali hydroxide is NaOH. In some embodiments, the aqueous $^{13}NH_3$-solution is transferred to a vessel containing the neat alkali hydroxide (e.g., NaOH) to release gaseous $^{13}NH_3$, such as through Teflon tubing with helium flow. In some embodiments, compound (IIa) is converted to compound (IIIa) in the presence of gaseous $^{13}NH_3$ at a temperature between about 0° C. and about 65° C. (such as about any of 0, 5, 10, 20, 30, 40, 50, 60, or 65° C., including any ranges between these values). In some embodiments, the released gaseous $^{13}NH_3$ is transferred to the reaction vessel containing compound (IIa). In some embodiments, the released gaseous $^{13}NH_3$ is transferred to the reaction vessel containing compound (IIa) manually by positive pressure, such as by using a syringe. Deprotection of the amine of compound (IIIa) provides the compound of formula (IV).

Another preparative embodiment of the preparative method in Scheme 1 is shown in Scheme 1b.

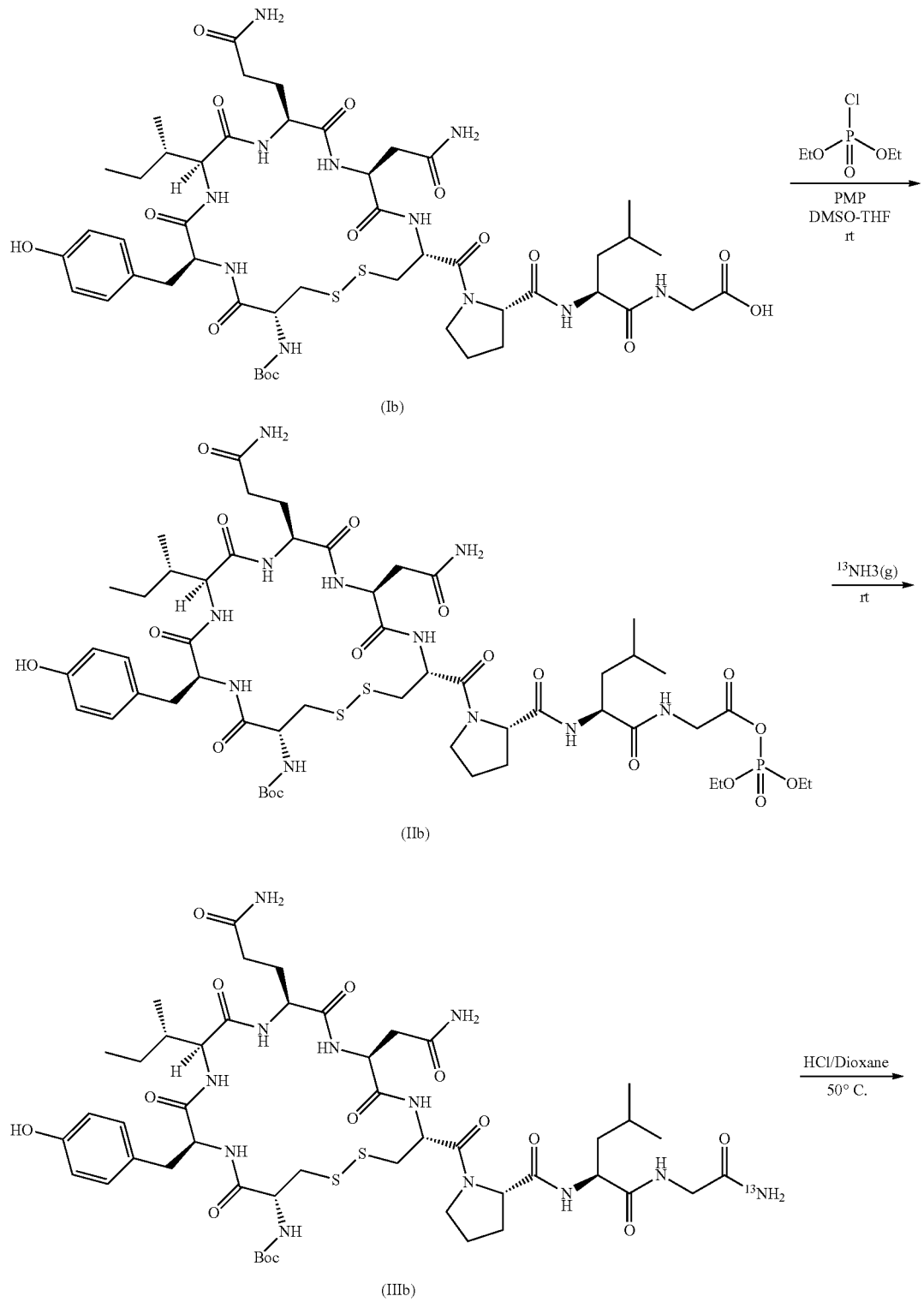

-continued

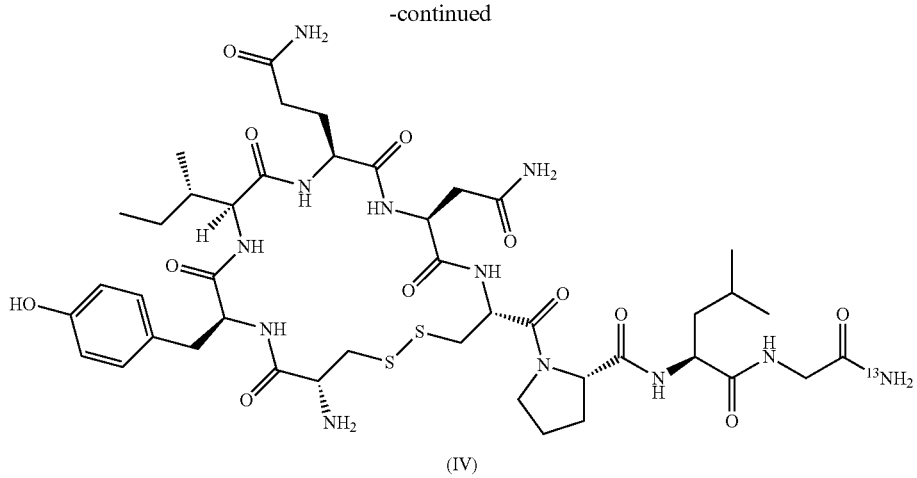

(IV)

Coupling of compound (Ib) with diethyl cyanophosphonate (DECP) provides intermediate compound (IIb). In some embodiments, compound (Ib) is coupled with DECP in the presence of dimethyl sulfoxide (DMSO), tetrahydrofuran (THF), and pentamethylpiperidine (PMP). In some embodiments, the DECP in the coupling reaction is between about 0.7 equivalents and about 1.1 equivalents (such as about any of 0.7, 0.8, 0.9, 1.0, and 1.1 equivalents). In some embodiments, the DECP in the coupling reaction is about 0.9 equivalents. In some embodiments, the ratio of DMSO to THE in the coupling reaction is between about 1:7 and about 1:11 (such as about any of 1:7, 1:8, 1:9, 1:10, and 1:11). In some embodiments, the ratio of DMSO to THE in the coupling reaction is about 1:9. In some embodiments, the coupling of compound (Ib) with DECP is carried out at a temperature between about 0° C. and about 65° C. (such as about any of 0, 5, 10, 20, 30, 40, 50, 60, or 65° C., including any ranges between these values). In some embodiments, coupling of compound (Ib) with DEPC is carried out in situ in a reaction vessel. In some embodiments, compound (Ib) is coupled with DECP in the presence of DMF/dioxane, DMF/THF, or DMSO/dioxane. Compound (IIb) is converted to compound (IIIb) in the presence of gaseous $^{13}NH_3$. In some embodiments, the gaseous $^{13}NH_3$ is produced by proton irradiation of a liquid target (e.g., $[^{16}O\ (p,\ \alpha)^{13}N]$) to form aqueous $^{13}NH_3$, followed by combining the aqueous $^{13}NH_3$ with neat alkali hydroxide (e.g., NaOH) to release gaseous $^{13}NH_3$. In some embodiments, the liquid target is $[^{16}O\ (p,\ \alpha)^{13}N]$. In some embodiments, the neat alkali hydroxide is NaOH. In some embodiments, the aqueous $^{13}NH_3$-solution is transferred to a vessel containing the neat alkali hydroxide (e.g., NaOH) to release gaseous $^{13}NH_3$, such as through Teflon tubing with helium flow. In some embodiments, compound (IIb) is converted to compound (IIIb) in the presence of gaseous $^{13}NH_3$ at a temperature between about 0° C. and about 65° C. (such as about any of 0, 5, 10, 20, 30, 40, 50, 60, or 65° C., including any ranges between these values). In some embodiments, the released gaseous $^{13}NH_3$ is transferred to the reaction vessel containing compound (IIb). In some embodiments, the released gaseous $^{13}NH_3$ is transferred to the reaction vessel containing compound (IIb) manually by positive pressure, such as by using a syringe. Deprotection of the amine of compound (IIIb) provides the compound of formula (IV). In some embodiments, compound (IIIb) is deprotected to provide compound (IV) in the presence of HCl and dioxane. In some embodiments, the HCl is at a concentration between about 3.5M and about 4.5M (such as about any of 3.5, 3.6, 3.7, 3.8, 3.9, 4.0, 4.1, 4.2, 4.3, 4.4, or 4.5 M). In some embodiments, the deprotection is carried out at a temperature between about 45° C. and about 55° C. (such as about any of 45, 46, 47, 48, 49, 50, 51, 52, 53, 54, or 55° C.). In some embodiments, the deprotection is carried out at about 50° C. In some embodiments, the deprotection is carried out for a period of time between about 1 minute and about 5 minutes (such as about any of 1, 1.5, 2, 2.5, 3, 3.5, 4, 4.5, or 5 minutes). In some embodiments, the deprotection is carried out for about 2.5 minutes. In some embodiments, compound (IIIb) is deprotected to provide compound (IV) in the presence of HCl (e.g., 2M HCl) in diethyl ether, HCl (e.g., 1M HCl) in THF/Dioxane, or HCl (e.g., 1M HCl) in MeOH.

In some embodiments, deprotection of compound (III), (IIIa), or (IIIb) provides a crude preparation of the compound of formula (IV). In some embodiments, the crude preparation of compound (IV) is purified to remove reagents, organic solvents, and/or precursors. In some embodiments, purification is by high performance liquid chromatography (HPLC) or solid-phase extraction (SPE). In some embodiments, purification is carried out in one step. In some embodiments, purification is carried out in a plurality of steps. For example, in some embodiments, purification comprises: a) applying the crude preparation of compound (IV) to a first hydrophobic SPE column, such that the $^{13}$N-oxytocin and precursor of the crude preparation are retained on the first hydrophobic SPE column; b) applying a solution comprising an aqueous ion-pairing reagent to the first hydrophobic SPE column, such that the $^{13}$N-oxytocin is eluted in a first eluate; c) applying the first eluate to a second hydrophobic SPE column, such that the $^{13}$N-oxytocin of the first eluate is retained on the second hydrophobic SPE column; and d) eluting the $^{13}$N-oxytocin in a second eluate. In some embodiments, the first and/or second hydrophobic SPE columns comprise a silica-based bonded phase with strong hydrophobicity, such as a Sep-Pak C18 cartridge (Waters). In some embodiments, the crude preparation is diluted prior to applying to the first hydrophobic SPE column. In some embodiments, the solution comprising an aqueous ion-pairing reagent comprises acetonitrile. In some embodiments, the solution comprising an aqueous ion-pairing reagent comprises acetonitrile at a concentration between about 15% and about 25% (such as about any of 15, 16, 17, 18, 19, 20, 21, 22, 23, 24, or 25%). In some embodiments, the first eluate is diluted prior to applying to the second hydrophobic SPE column.

Methods of Use

Imaging

In some embodiments, there is provided a method for in vivo imaging of exogenously administered oxytocin in a subject. The method includes the steps of: (a) administering to the subject an $^{13}$N-labeled oxytocin peptide according to any of the embodiments described herein; (b) waiting a time sufficient to allow the $^{13}$N-labeled oxytocin peptide to accumulate at a tissue or cell site to be imaged; and (c) imaging the cells or tissues with a non-invasive imaging technique. The non-invasive imaging technique may be positron emission tomography imaging, or positron emission tomography with computed tomography imaging, or positron emission tomography with magnetic resonance imaging. In some embodiments, the $^{13}$N-oxytocin peptide is the compound of Formula (IV). In some embodiments, the $^{13}$N-labeled oxytocin is administered by craniofacial mucosal administration (e.g., nasal, buccal, or sublingual administration), e.g., for imaging central nervous system (CNS) tissue. In some embodiments, the $^{13}$N-labeled oxytocin is administered intranasally. In some embodiments, the $^{13}$N-labeled oxytocin is administered intravenously, intraarterially, intraperitoneally, intravesicularly, subcutaneously, intrathecally, intrapulmonarily, intramuscularly, intratracheally, ocularly (e.g., intraocularly), transdermally, or by suppository, e.g., for imaging of peripheral tissue. In some embodiments, the $^{13}$N-labeled oxytocin is administered intravenously.

In some embodiments, according to any of the methods described herein comprising administration of an $^{13}$N-labeled oxytocin peptide, the $^{13}$N-labeled oxytocin peptide is co-administered with a non-radiolabeled oxytocin peptide. In some embodiments, the $^{13}$N-labeled oxytocin peptide and the non-radiolabeled oxytocin peptide are contained in a single formulation or composition. In some embodiments, the $^{13}$N-labeled oxytocin peptide and the non-radiolabeled oxytocin peptide are contained in separate formulations or compositions. In some embodiments, the method further comprises a step of administering an amount (e.g., an effective amount) of a composition comprising non-radiolabeled oxytocin. In some embodiments, the administration of the non-radiolabeled oxytocin is carried out before administration of the $^{13}$N-labeled oxytocin peptide, e.g., at least about 10 min (such as at least about any of 10 min, 20 min, 30 min, 45 min, 1 h, 2 h, 3 h, 4 h, or more, including any ranges between these values) before administration of the $^{13}$N-labeled oxytocin peptide. In some embodiments, the administration of the non-radiolabeled oxytocin is carried out after administration of the $^{13}$N-labeled oxytocin peptide, e.g., at least about 10 min (such as at least about any of 10 min, 20 min, 30 min, 45 min, 1 h, 2 h, 3 h, 4 h, or more, including any ranges between these values) after administration of the $^{13}$N-labeled oxytocin peptide. In some embodiments, the administration of the non-radiolabeled oxytocin is carried out after administration of the $^{13}$N-labeled oxytocin peptide, e.g., at least about 10 min (such as at least about any of 10 min, 20 min, 30 min, 45 min, 1 h, 2 h, 3 h, 4 h, or more, including any ranges between these values) after administration of the $^{13}$N-labeled oxytocin peptide, and the method further comprises repeating steps (a), (b), and (c) after administration of the non-radiolabeled oxytocin, e.g., at least about 10 min (such as at least about any of 10 min, 20 min, 30 min, 45 min, 1 h, 2 h, 3 h, 4 h, or more, including any ranges between these values) after administration of the non-radiolabeled oxytocin. In some embodiments, where two doses of the $^{13}$N-labeled oxytocin peptide are administered, the time interval between administrations of the two doses of the $^{13}$N-labeled oxytocin peptide is at least about 20 min (such as at least about any of 20 min, 30 min, 45 min, 1 h, 2 h, 3 h, 4 h, or more, including any ranges between these values). In some embodiments, the method further comprises administration of one or more additional doses (e.g., effective doses) of non-radiolabeled oxytocin. In some embodiments, where the non-radiolabeled oxytocin is administered separately from the $^{13}$N-labeled oxytocin, the non-radiolabeled oxytocin is administered by the same route as the $^{13}$N-labeled oxytocin. In some embodiments, where the non-radiolabeled oxytocin is administered separately from the $^{13}$N-labeled oxytocin, the non-radiolabeled oxytocin is administered by a different route than the $^{13}$N-labeled oxytocin. In some embodiments, the non-radiolabeled oxytocin is administered by craniofacial mucosal administration (e.g., nasal, buccal, or sublingual administration). In some embodiments, the non-radiolabeled oxytocin is administered intranasally. In some embodiments, the non-radiolabeled oxytocin is administered intravenously, intraarterially, intraperitoneally, intravesicularly, subcutaneously, intrathecally, intrapulmonarily, intramuscularly, intratracheally, ocularly (e.g., intraocularly), transdermally, or by suppository. In some embodiments, the non-radiolabeled oxytocin is administered intravenously.

In some embodiments, according to any of the methods described herein comprising administration of an $^{13}$N-labeled oxytocin peptide, the $^{13}$N-labeled oxytocin peptide is co-administered with another agent. In some embodiments, the other agent affects the distribution, kinetics, and/or pharmacodynamics of oxytocin. In some embodiments, the other agent is a divalent metal cation (e.g., $Mg^{2+}$, $Ca^{2+}$, $Zn^{2+}$, or $Cu^{2+}$). In some embodiments, the divalent metal cation is $Mg^{2+}$. In some embodiments, the other agent is vasopressin. In some embodiments, the $^{13}$N-labeled oxytocin peptide and the other agent are contained in a single formulation or composition. For example, in some embodiments, the method comprises administration of a formulation or composition comprising the $^{13}$N-labeled oxytocin peptide and a divalent metal cation (e.g., $Mg^{2+}$, $Ca^{2+}$, $Zn^{2+}$, or $Cu^{2+}$) or vasopressin. In some embodiments, the $^{13}$N-labeled oxytocin peptide and the other agent are contained in separate formulations or compositions. For example, in some embodiments, the method comprises administration of a formulation or composition comprising the $^{13}$N-labeled oxytocin peptide and administration of a formulation or composition comprising a divalent metal cation (e.g., $Mg^{2+}$, $Ca^{2+}$, $Zn^{2+}$, or $Cu^{2+}$) or vasopressin. In some embodiments, the other agent is administered concurrently with the $^{13}$N-labeled oxytocin peptide. In some embodiments, the other agent and the $^{13}$N-labeled oxytocin peptide are administered sequentially. In some embodiments, the other agent is administered before the $^{13}$N-labeled oxytocin peptide. In some embodiments, the other agent is administered after the $^{13}$N-labeled oxytocin peptide. In some embodiments, where the other agent is administered separately from the $^{13}$N-labeled oxytocin, the other agent is administered by the same route as the $^{13}$N-labeled oxytocin. In some embodiments, where the other agent is administered separately from the $^{13}$N-labeled oxytocin, the other agent is administered by a different route than the $^{13}$N-labeled oxytocin. In some embodiments, the other agent is administered by craniofacial mucosal administration (e.g., nasal, buccal, or sublingual administration). In some embodiments, the other agent is administered intranasally. In some embodiments, the other agent is administered intravenously, intraarterially, intraperitoneally, intravesicularly, subcutaneously, intrathecally, intrapulmonarily, intramuscularly, intratracheally, ocularly (e.g., intraocularly), transdermally, or by suppository. In some embodiments, the other agent is administered intravenously.

In some embodiments, there is provided a method of imaging of exogenously administered oxytocin in a subject by emission tomography. The method includes the steps of: (a) administering to the subject an $^{13}$N-labeled oxytocin peptide according to any of the embodiments described herein; (b) using a plurality of detectors to detect gamma rays emitted from the subject and to communicate signals corresponding to the detected gamma rays; and (c) reconstructing from the signals a series of medical images of a region of interest of the subject. In some embodiments, the $^{13}$N-oxytocin peptide is the compound of Formula (IV). In some embodiments, the $^{13}$N-oxytocin peptide is administered by craniofacial mucosal administration (e.g., intranasal administration). In some embodiments, the $^{13}$N-oxytocin peptide is administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided an imaging method comprising acquiring an image of a human patient to whom a detectable amount of an $^{13}$N-labeled oxytocin peptide according to any of the embodiments described herein has been administered. The method may comprise acquiring an image (e.g., a brain image) of the patient using positron emission tomography imaging, positron emission tomography with computed tomography imaging, or positron emission tomography with magnetic resonance imaging. The detectable amount of the $^{13}$N-labeled oxytocin peptide is an amount that is sufficient to enable detection of accumulation of the $^{13}$N-labeled oxytocin peptide in cells or tissue by a medical imaging technique. In some embodiments, the $^{13}$N-oxytocin peptide is the compound of Formula (IV). In some embodiments, the $^{13}$N-oxytocin peptide is administered by craniofacial mucosal administration (e.g., intranasal administration). In some embodiments, the $^{13}$N-oxytocin peptide is administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided a method for determining the distribution of exogenously administered oxytocin in a subject. In some embodiments, the method comprises: (a) administering to the subject an $^{13}$N-labeled oxytocin peptide according to any of the embodiments described herein; (b) allowing the $^{13}$N-labeled oxytocin peptide to accumulate at a tissue or cell site to be imaged; and (c) imaging the cells or tissues with a non-invasive imaging technique. The non-invasive imaging technique may be positron emission tomography imaging, or positron emission tomography with computed tomography imaging, or positron emission tomography with magnetic resonance imaging. In some embodiments, the $^{13}$N-oxytocin peptide is the compound of Formula (IV). In some embodiments, the $^{13}$N-oxytocin peptide is administered by craniofacial mucosal administration (e.g., intranasal administration). In some embodiments, the $^{13}$N-oxytocin peptide is administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided a method for determining the distribution of oxytocin receptors in a subject. In some embodiments, the method comprises: (a) administering to the subject an $^{13}$N-labeled oxytocin peptide according to any of the embodiments described herein; (b) allowing the $^{13}$N-labeled oxytocin peptide to bind to oxytocin receptors; and (c) imaging the $^{13}$N-labeled oxytocin peptide in the individual with a non-invasive imaging technique. The non-invasive imaging technique may be positron emission tomography imaging, or positron emission tomography with computed tomography imaging, or positron emission tomography with magnetic resonance imaging. In some embodiments, the $^{13}$N-oxytocin peptide is the compound of Formula (IV). In some embodiments, the $^{13}$N-oxytocin peptide is administered by craniofacial mucosal administration (e.g., intranasal administration).

In some embodiments, the $^{13}$N-oxytocin peptide is administered intravenously, intraarterially, intraperitoneally, intravesicularly, subcutaneously, intrathecally, intrapulmonarily, intramuscularly, intratracheally, ocularly (e.g., intraocularly), transdermally, or by suppository. In some embodiments, there is provided a method for determining the kinetics of exogenously administered oxytocin in an individual. In some embodiments, the method comprises: (a) administering to the subject an $^{13}$N-labeled oxytocin peptide according to any of the embodiments described herein; and (b) imaging the $^{13}$N-labeled oxytocin peptide in the individual over a period of time with a non-invasive imaging technique. The non-invasive imaging technique may be positron emission tomography imaging, or positron emission tomography with computed tomography imaging, or positron emission tomography with magnetic resonance imaging. In some embodiments, the $^{13}$N-oxytocin peptide is the compound of Formula (IV). In some embodiments, the $^{13}$N-oxytocin peptide is administered by craniofacial mucosal administration (e.g., intranasal administration). In some embodiments, the $^{13}$N-oxytocin peptide is administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

Emission Tomography

In some embodiments, the methods described herein employ an emission tomography system for acquiring a series of medical images of a subject during an imaging process using an $^{13}$N-labeled oxytocin peptide as a radiotracer. In some embodiments, the system includes a plurality of detectors configured to be arranged about the subject to acquire gamma rays emitted from the subject over a time period relative to an administration of the $^{13}$N-labeled oxytocin peptide to the subject and communicate signals corresponding to acquired gamma rays; a data processing system configured to receive the signals from the plurality of detectors; and a reconstruction system configured to receive the signals from the data processing system and reconstruct therefrom a series of medical images of the subject. The $^{13}$N-labeled oxytocin peptide may be any of the $^{13}$N-labeled oxytocin peptides described herein.

Treatment

In some embodiments, there is provided a method of treating a disorder or condition including psychiatric, neuropsychiatric, and psychological disorders, inflammatory conditions, and pain comprising administering to an individual in need thereof an effective dose of an oxytocin peptide formulation, wherein administration of the oxytocin peptide formulation results in distribution and/or kinetics of the oxytocin peptide in the individual favorable for the treatment of the disorder or condition. In some embodiments, the distribution and/or kinetics of the oxytocin peptide in the individual is determined by administering to the individual an $^{13}$N-oxytocin peptide formulation or composition comprising $^{13}$N-labeled oxytocin and imaging the $^{13}$N-labeled oxytocin peptide in the individual according to any of the embodiments described herein, such as by PET. In some embodiments, the oxytocin peptide formulation further comprises non-radiolabeled oxytocin. In some embodiments, the oxytocin peptide formulation comprises an effective amount of oxytocin (including $^{13}$N-labeled oxytocin and non-radiolabeled oxytocin) for treating the disorder or condition. In some embodiments, the oxytocin peptide formulation comprises a) an effective amount of non-radiolabeled oxytocin; and b) an amount of $^{13}$N-labeled oxytocin suitable for use as an imaging tracer, e.g., a PET tracer. In some embodiments, the oxytocin peptide formulation is administered by craniofacial mucosal administration (e.g., intranasal administration). In some embodiments, the oxytocin peptide formulation is administered intravenously, intraarterially, intraperitoneally, intravesicularly, subcutaneously, intrathecally, intrapulmonarily, intramuscularly, intratracheally, ocularly (e.g., intraocularly), transdermally, or by suppository. In some embodiments, the neuropsychiatric disorder includes autism spectrum disorder, disorders manifesting one or more symptoms associated with autism spectrum disorder, social and communication deficits, and anxiety disorders. In some embodiments, the pain includes orofacial and craniofacial pain (e.g., headache pain), neck pain (e.g. occipital neuralgia), and pain in the upper extremities.

For example, in some embodiments, there is provided a method of treating a pain and/or an inflammatory condition comprising administering to an individual in need thereof an effective dose of an oxytocin peptide formulation, wherein administration of the oxytocin peptide formulation results in distribution of the oxytocin peptide to nasal mucosa innervated by the trigeminal nerve. In some embodiments, the distribution of the oxytocin peptide in the individual is determined by administering to the individual an $^{13}$N-oxytocin peptide formulation or composition comprising $^{13}$N-labeled oxytocin and imaging the $^{13}$N-labeled oxytocin peptide in the individual according to any of the embodiments described herein, such as by PET. In some embodiments, the oxytocin peptide formulation is administered by craniofacial mucosal administration (e.g., intranasal administration). In some embodiments, the oxytocin peptide formulation is administered intravenously. In some embodiments, the pain includes orofacial and craniofacial pain (e.g., headache pain), neck pain (e.g. occipital neuralgia), and pain in the upper extremities.

In some embodiments, there is provided a method of treating a psychiatric, neuropsychiatric, or psychological disorder comprising administering to an individual in need thereof an effective dose of an oxytocin peptide formulation, wherein administration of the oxytocin peptide formulation results in distribution of the oxytocin peptide to nasal mucosa innervated by the olfactory nerve (e.g., the superior-most portion of the mucosa). In some embodiments, the distribution of the oxytocin peptide in the individual is determined by administering to the individual the oxytocin peptide formulation or composition spiked with a detectable amount of $^{13}$N-labeled oxytocin and imaging the $^{13}$N-labeled oxytocin peptide in the individual according to any of the embodiments described herein, such as by PET. In some embodiments, the oxytocin peptide formulation is administered by craniofacial mucosal administration (e.g., intranasal administration). In some embodiments, the oxytocin peptide formulation is administered intravenously. In some embodiments, the neuropsychiatric disorder includes autism spectrum disorder, disorders manifesting one or more symptoms associated with autism spectrum disorder, social and communication deficits, and anxiety disorders.

In some embodiments, there is provided a method of assessing an oxytocin peptide formulation for treating a disorder or condition including psychiatric, neuropsychiatric, and psychological disorders, inflammatory conditions, and pain in an individual, comprising a) administering the oxytocin peptide formulation to the individual, wherein the oxytocin peptide formulation comprises $^{13}$N-labeled oxytocin; b) determining the distribution and/or kinetics of the $^{13}$N-labeled oxytocin in the individual according to any of the embodiments described herein; and c) assessing the oxytocin peptide formulation based on the favorability of the distribution and/or kinetics of the $^{13}$N-labeled oxytocin in the individual for treating the disorder or condition. In some embodiments, the oxytocin peptide formulation further comprises non-radiolabeled oxytocin. In some embodiments, the oxytocin peptide formulation comprises an effective amount of oxytocin (including $^{13}$N-labeled oxytocin and non-radiolabeled oxytocin) for treating the disorder or condition. In some embodiments, the oxytocin peptide formulation comprises a) an effective amount of non-radiolabeled oxytocin; and b) an amount of $^{13}$N-labeled oxytocin suitable for use as an imaging tracer, e.g., a PET tracer. In some embodiments, the oxytocin peptide formulation is administered by craniofacial mucosal administration (e.g., intranasal administration). In some embodiments, the oxytocin peptide formulation is administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided a method of assessing an oxytocin peptide formulation for treating a disorder or condition including psychiatric, neuropsychiatric, and psychological disorders, inflammatory conditions, and pain, comprising a) administering the oxytocin peptide formulation to a plurality of individuals, wherein the oxytocin peptide formulation comprises $^{13}$N-labeled oxytocin; b) determining the distribution and/or kinetics of the $^{13}$N-labeled oxytocin in the plurality of individuals according to any of the embodiments described herein; and c) assessing the oxytocin peptide formulation based on the favorability of the distribution and/or kinetics of the $^{13}$N-labeled oxytocin in the plurality of individuals for treating the disorder or condition. In some embodiments, the oxytocin peptide formulation further comprises non-radiolabeled oxytocin. In some embodiments, the oxytocin peptide formulation comprises an effective amount of oxytocin (including $^{13}$N-labeled oxytocin and non-radiolabeled oxytocin) for treating the disorder or condition. In some embodiments, the oxytocin peptide formulation comprises a) an effective amount of non-radiolabeled oxytocin; and b) an amount of $^{13}$N-labeled oxytocin suitable for use as an imaging tracer, e.g., a PET tracer. In some embodiments, the oxytocin peptide formulation is administered by craniofacial mucosal administration (e.g., intranasal administration). In some embodiments, the oxytocin peptide formulation is administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided a method of selecting an oxytocin peptide formulation for treating a disorder or condition including psychiatric, neuropsychiatric, and psychological disorders, inflammatory conditions, and pain in an individual, comprising a) administering a plurality of oxytocin peptide formulations to an individual, wherein the oxytocin peptide formulations comprise $^{13}$N-labeled oxytocin; b) determining the distribution and/or kinetics of the $^{13}$N-labeled oxytocin in the individual for each of the plurality of oxytocin peptide formulations according to any of the embodiments described herein; and c) selecting the oxytocin peptide formulation with the most favorable distribution and/or kinetics of the $^{13}$N-labeled oxytocin in the individual for treating the disorder or condition. In some embodiments, the oxytocin peptide formulations further comprise non-radiolabeled oxytocin. In some embodiments, the oxytocin peptide formulations comprise an effective amount of oxytocin (including $^{13}$N-labeled oxytocin and non-radiolabeled oxytocin) for treating the disorder or condition. In some embodiments, the oxytocin peptide formulations comprise a) an effective amount of non-radiolabeled oxytocin; and b) an amount of $^{13}$N-labeled oxytocin suitable for use as an imaging tracer, e.g., a PET tracer. In some embodiments, the oxytocin peptide formulations are administered by craniofacial mucosal administration (e.g., intranasal administration). In some embodiments, the oxytocin peptide formulations are administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided a method of selecting an oxytocin peptide formulation for treating a disorder or condition including psychiatric, neuropsychiatric, and psychological disorders, inflammatory conditions, and pain, comprising a) administering a plurality of oxytocin peptide formulations to a plurality of individuals, wherein the oxytocin peptide formulations comprise $^{13}$N-labeled oxytocin; b) determining the distribution and/or kinetics of the $^{13}$N-labeled oxytocin in each of the plurality of individuals for each of the plurality of oxytocin peptide formulations according to any of the embodiments described herein; and c) selecting the oxytocin peptide formulation with the most favorable distribution and/or kinetics of the $^{13}$N-labeled oxytocin in the plurality of individuals for treating the disorder or condition. In some embodiments, the oxytocin peptide formulations further comprises non-radiolabeled oxytocin. In some embodiments, the oxytocin peptide formulations comprise an effective amount of oxytocin (including $^{13}$N-labeled oxytocin and non-radiolabeled oxytocin) for treating the disorder or condition. In some embodiments, the oxytocin peptide formulations comprise a) an effective amount of non-radiolabeled oxytocin; and b) an amount of $^{13}$N-labeled oxytocin suitable for use as an imaging tracer, e.g., a PET tracer. In some embodiments, the oxytocin peptide formulations are administered by craniofacial mucosal administration (e.g., intranasal administration). In some embodiments, the oxytocin peptide formulations are administered intravenously, intraarterially, intraperitoneally, intravesicularly, subcutaneously, intrathecally, intrapulmonarily, intramuscularly, intratracheally, ocularly (e.g., intraocularly), transdermally, or by suppository.

In some embodiments, there is provided a method of assessing a therapy for treating a disorder or condition including psychiatric, neuropsychiatric, and psychological disorders, inflammatory conditions, and pain in an individual comprising administration of an oxytocin peptide formulation, comprising a) treating an individual with the therapy, wherein the oxytocin peptide formulation comprises $^{13}$N-labeled oxytocin; b) determining the distribution and/or kinetics of the $^{13}$N-labeled oxytocin in the individual according to any of the embodiments described herein; and c) assessing the therapy based on the favorability of the distribution and/or kinetics of the $^{13}$N-labeled oxytocin in the individual for treating the disorder or condition. In some embodiments, the oxytocin peptide formulation further comprises non-radiolabeled oxytocin. In some embodiments, the oxytocin peptide formulation comprises an effective amount of oxytocin (including $^{13}$N-labeled oxytocin and non-radiolabeled oxytocin) for treating the disorder or condition. In some embodiments, the oxytocin peptide formulation comprises a) an effective amount of non-radiolabeled oxytocin; and b) an amount of $^{13}$N-labeled oxytocin suitable for use as an imaging tracer, e.g., a PET tracer. The therapy may include an oxytocin peptide formulation according to any of the formulations described herein, such as those described in the section titled "Oxytocin peptide formulation," administered by any of the methods of administration described herein, such as those described in the section titled "Oxytocin administration."

In some embodiments, there is provided a method of assessing a therapy for treating a disorder or condition including psychiatric, neuropsychiatric, and psychological disorders, inflammatory conditions, and pain comprising administration of an oxytocin peptide formulation, comprising a) treating a plurality of individuals with the therapy, wherein the oxytocin peptide formulation comprises $^{13}$N-labeled oxytocin; b) determining the distribution and/or kinetics of the $^{13}$N-labeled oxytocin in the plurality of individuals according to any of the embodiments described herein; and c) assessing the therapy based on the favorability of the distribution and/or kinetics of the $^{13}$N-labeled oxytocin in the plurality of individuals for treating the disorder or condition. In some embodiments, the oxytocin peptide formulation further comprises non-radiolabeled oxytocin. In some embodiments, the oxytocin peptide formulation comprises an effective amount of oxytocin (including $^{13}$N-labeled oxytocin and non-radiolabeled oxytocin) for treating the disorder or condition. In some embodiments, the oxytocin peptide formulation comprises a) an effective amount of non-radiolabeled oxytocin; and b) an amount of $^{13}$N-labeled oxytocin suitable for use as an imaging tracer, e.g., a PET tracer. The therapy may include an oxytocin peptide formulation according to any of the formulations described herein, such as those described in the section titled "Oxytocin peptide formulation," administered by any of the methods of administration described herein, such as those described in the section titled "Oxytocin administration."

In some embodiments, there is provided a method of selecting a therapy for treating a disorder or condition including psychiatric, neuropsychiatric, and psychological disorders, inflammatory conditions, and pain in an individual comprising administration of an oxytocin peptide formulation, comprising a) treating an individual with a plurality of therapies comprising administration of an oxytocin peptide formulation, wherein the oxytocin peptide formulations comprise $^{13}$N-labeled oxytocin; b) determining the distribution and/or kinetics of the $^{13}$N-labeled oxytocin in the individual for each of the plurality of therapies according to any of the embodiments described herein; and c) selecting the therapy with the most favorable distribution and/or kinetics of the $^{13}$N-labeled oxytocin in the individual for treating the disorder or condition. In some embodiments, the oxytocin peptide formulations further comprise non-radiolabeled oxytocin. In some embodiments, the oxytocin peptide formulations comprise an effective amount of oxytocin (including $^{13}$N-labeled oxytocin and non-radiolabeled oxytocin) for treating the disorder or condition. In some embodiments, the oxytocin peptide formulations comprise a) an effective amount of non-radiolabeled oxytocin; and b) an amount of $^{13}$N-labeled oxytocin suitable for use as an imaging tracer, e.g., a PET tracer. The therapies may include an oxytocin peptide formulation according to any of the formulations described herein, such as those described in the section titled "Oxytocin peptide formulation," administered by any of the methods of administration described herein, such as those described in the section titled "Oxytocin administration."

In some embodiments, there is provided a method of selecting a therapy for treating a disorder or condition including psychiatric, neuropsychiatric, and psychological disorders, inflammatory conditions, and pain comprising administration of an oxytocin peptide formulation, comprising a) treating a plurality of individuals with a plurality of therapies comprising administration of an oxytocin peptide formulation, wherein the oxytocin peptide formulations comprise $^{13}$N-labeled oxytocin; b) determining the distribution and/or kinetics of the $^{13}$N-labeled oxytocin in each of the plurality of individuals for each of the plurality of therapies according to any of the embodiments described herein; and c) selecting the therapy with the most favorable distribution and/or kinetics of the $^{13}$N-labeled oxytocin in the plurality of individuals for treating the disorder or condition. In some embodiments, the oxytocin peptide formulations further comprises non-radiolabeled oxytocin. In some embodiments, the oxytocin peptide formulations comprise an effective amount of oxytocin (including $^{13}$N-labeled oxytocin and non-radiolabeled oxytocin) for treating the disorder or condition. In some embodiments, the oxytocin peptide formulations comprise a) an effective amount of non-radiolabeled oxytocin; and b) an amount of $^{13}$N-labeled oxytocin suitable for use as an imaging tracer, e.g., a PET tracer. The therapies may include an oxytocin peptide formulation according to any of the formulations described herein, such as those described in the section titled "Oxytocin peptide formulation," administered by any of the methods of administration described herein, such as those described in the section titled "Oxytocin administration."

Diseases and Conditions

The terms "autism spectrum disorder (ASD)" or "autism" refer to a group of complex disorders of brain development. These disorders are characterized, in varying degrees, by difficulties in social interaction, verbal and nonverbal communication and repetitive behaviors. With the May 2013 publication of the fifth edition of the Diagnostic and Statistical Manual of Mental Disorders (DSM-5), all autism disorders were merged into one umbrella diagnosis of ASD. Previously, they were recognized as distinct subtypes, including autistic disorder, childhood disintegrative disorder, pervasive developmental disorder-not otherwise specified (PDD-NOS) and Asperger syndrome. See http://www.autismspeaks.org/what-autism. Those skilled in the art will recognize that there is considerable overlap of the symptoms of autism spectrum disorder with many other psychiatric disorders. Examples of disorders which exhibit symptoms similar to those displayed in autism spectrum disorder include, but are not limited to, social anxiety disorder, obsessive-compulsive disorder, social (pragmatic) communication disorder, and neurodevelopmental disorders including but not limited to attention deficit hyperactivity disorder, Prader-Willi syndrome, Timothy syndrome, Fragile-X syndrome, Rett syndrome, and Williams syndrome.

Autism spectrum disorders (ASD) are characterized by social-interaction difficulties, communication challenges and a tendency to engage in repetitive behaviors. However, symptoms and their severity vary widely across these three core areas. ASD can be associated with intellectual disability, difficulties in motor coordination and attention and physical health issues such as sleep and gastrointestinal disturbances. ASD can be associated with psychiatric symptoms including anxiety and depression. See, e.g., Kim et al., *Autism* 2000, 4(2):117-132.

Oxytocin has been known to treat a number of conditions including anxiety and social and communication deficits in autism spectrum disorders. However, it has been observed that the effect of oxytocin in treating social and communication deficits in autism spectrum disorder varies widely between patients. It is possible that variations in receptor availability and receptor affinity for oxytocin are responsible for the variation in effect. Clinical efforts in using commercial formulations of oxytocin (e.g., Syntocinon®) to treat ASD have been marred by lack of efficacy and poor tolerability. Due to the low potency and high volume of currently available oxytocin formulations, when administered by nasal spray, the amount of drug absorbed is insufficient for efficacy. The present invention in some embodiments provides a method for evaluating an oxytocin peptide therapy for treating an autism spectrum disorder, a disorder manifesting one or more symptoms associated with an autism spectrum disorder, social and communication deficits, or an anxiety disorder.

In some embodiments, according to any of the methods described herein, the subject suffers from an autism spectrum disorder, a disorder manifesting one or more symptoms associated with an autism spectrum disorder, social and communication deficits, or an anxiety disorder. Examples of symptoms associated with an autism spectrum disorder include but are not limited to persistent deficits in social communication and social interaction, social anxiety, and restricted repetitive behaviors, interests and activities. Other behaviors and characteristics also observed in persons with autism spectrum disorder include an aversion to physical contact, generalized anxiety, a monotone voice or an inability to modulate volume of voice, failure to develop peer relationships, lack of shared enjoyment and interests and lack of social or emotional reciprocity. Examples of disorders which exhibit symptoms similar to those displayed in autism spectrum disorder include, but are not limited to, social anxiety disorder, obsessive-compulsive disorder, social (pragmatic) communication disorder, and neurodevelopmental disorders including but not limited to attention deficit hyperactivity disorder, Prader-Willi syndrome, Timothy syndrome, Fragile-X syndrome, Rett syndrome, and Williams syndrome.

In some embodiments, according to any of the methods described herein, the subject suffers from Prader-Willi syndrome. Prader-Willi Syndrome is a complex genetic condition that affects many parts of the body and is caused by a loss of function of genes in a particular region of chromosome 15. Individuals with Prader-Willi Syndrome often have mild to moderate intellectual impairment and learning difficulties and many exhibit behavioral problems including temper outbursts, stubbornness, manipulative behavior, and obsessive-compulsive behaviors including skin picking. Other symptoms often observed in individuals with Prader-Willi Syndrome are persistent deficits in social communication and social interaction, anxiety and irritability, and sleep problems. In some embodiments, In some embodiments, according to any of the methods described herein, the subject suffers from one or more symptoms associated with Prader-Willi syndrome. Examples of symptoms associated with Prader-Willi syndrome include but are not limited to persistent deficits in social communication and social interaction, anxiety and irritability, and sleep problems. In some embodiments, according to any of the methods described herein, the subject suffers from anxiety associated with Prader-Willi syndrome.

In some embodiments, according to any of the methods described herein, the subject suffers from social and communication deficits. In some embodiments, the social and communication deficits is an impairment in communication skills and/or social interaction, a lack of eye contact, and/or an inability to form and/or maintain social relationships.

In some embodiments, according to any of the methods described herein, the subject suffers from anxiety associated with autism spectrum disorder.

In some embodiments, according to any of the methods described herein, the subject suffers from pain, including, without limitation, orofacial and craniofacial pain (e.g., headache pain), neck pain (e.g. occipital neuralgia), and pain in the upper extremities. In some embodiments, the pain is a somatic pain. In some embodiments, the pain is a superficial somatic pain. In some embodiments, the pain is a deep somatic pain. In some embodiments, the pain is a musculoskeletal pain. In some embodiments, the pain is a visceral pain. In some embodiments, the pain is a neuropathic pain. In some embodiments, the pain is a head pain or a craniofacial pain. In some embodiments, the pain is in parts of the body other than the head and/or orofacial region. In some embodiments, the pain is a chronic pain such as a chronic pain described herein. In some embodiments, the pain is an acute pain such as an acute pain described herein. In some embodiments, the pain is a combination of one or more of the pain described herein. In some embodiment, the pain is a sharp and shooting pain associated with movement. In some embodiments, the pain is a neuropathic pain is caused by nerve injury, such as surgery related nerve injury.

In some embodiments, the pain is a head pain. In some embodiments, the pain is a facial pain. In some embodiments, the pain is a neck pain. In some embodiments, the pain is an occipital neuralgia. In some embodiments, the pain is a pain in the upper extremities. Neck and upper extremity pain includes but is not limited to examples such as nerve compression disorders (spinal stenosis), disc and vertebral diseases, diabetic neuropathy, carpal tunnel syndrome, arthritic disease, post-trauma, facet disorders, and post-herpetic neuralgia. In some embodiments, the pain is exacerbated by a psychiatric disorder, such as depression, anxiety or stress. In some embodiments, the pain is induced or exacerbated by food (e.g., caffeine, chocolate, alcohol) or by medication overuse (e.g., opiates).

In some embodiments, the pain is a trigeminal nerve-associated pain. The trigeminal nerve-associated pain may be selected from the group consisting of chronic, acute and procedural-related pain and combinations thereof. In some embodiments, the chronic pain is selected from the group consisting of trigeminal neuralgia, atypical facial pain, anesthesia dolorosa, post-herpetic neuralgia, cancer of the head and neck, migraine headaches, and temporomandibular joint pain (TMJ). In some embodiments, the procedural-related pain is pain arising from dental, medical, surgical or cosmetic procedures. In some embodiments, the acute pain is pain arising from a laceration, a burn, a broken bone, an injury, a headache, an abscessed tooth, dental disease, a bacterial infection or a sinus infection. Chronic, acute or procedural pain associated with the trigeminal nerve system is experienced in many syndromes and diseases including, but not limited to, trigeminal neuralgia, atypical facial pain, anesthesia dolorosa, post-herpetic neuralgia, cancer of the head and neck, migraine headaches, other types of headaches, TMJ, injuries to the face and/or head, injuries or infections of the teeth, common dental procedures and facial surgeries such as cosmetic plastic surgery.

Chronic pain in the face and head region can arise from a variety of medical conditions including but not limited to neuropathic pain, headache pain, TMJ, pain from cancer and/or cancer treatment. These pain syndromes are often not effectively treated with current medications or invasive interventions and new methods for localized pain relief in the face and head regions are needed.

In some embodiments, the $^{13}$N-oxytocin peptide formulation or composition described herein is targeted to the trigeminal nerve system. In some embodiments, the $^{13}$N-oxytocin peptide formulation or composition is administered to a subject suffering from any of the diseases and conditions described herein.

In some embodiments of the methods described herein, the individual is a mammal. In some embodiments, the individual is human.

Oxytocin Peptide Formulations

In some embodiments, there is provided an $^{13}$N-oxytocin peptide formulation and uses thereof in determining the distribution and kinetics of oxytocin following craniofacial mucosal application (such as nasal application) of the $^{13}$N-oxytocin peptide formulation. In some embodiments, the $^{13}$N-oxytocin peptide formulation comprises another agent. In some embodiments, the other agent is non-radiolabeled oxytocin. In some embodiments, the other agent affects the distribution, kinetics, and/or pharmacodynamics of oxytocin. In some embodiments, the other agent is a divalent metal cation (e.g., $Mg^{2+}$, $Ca^{2+}$, $Zn^{2+}$, or $Cu^{2+}$). In some embodiments, the divalent metal cation is $Mg^{2+}$. In some embodiments, the other agent is vasopressin.

Oxytocin has been known to treat head and craniofacial pain in humans and rats, and in the upper extremities of rats when administered intranasally, being particularly effective in the treatment of chronic pain where oxytocin receptors are overexpressed. However, it has been observed that the analgesic effect of oxytocin in treating head pain, for example, migraine headache pain in human patients, does not occur immediately after administration. Rather an initial period of up to 2 hours is required before onset of significant analgesia and 4 hours to maximal analgesic effect, while the patient continues to suffer from the pain during this initial period. Various components of oxytocin formulations, such as magnesium or other divalent cations, can affect oxytocin therapy, including modulation of the reduction in pain intensity and onset and/or duration of the analgesic effect.

In some embodiments, the $^{13}$N-oxytocin peptide formulation or composition is a liquid formulation comprising between about 0.01 mg/mL and about 16 mg/mL of oxytocin (including $^{13}$N-oxytocin peptide and non-radiolabeled oxytocin). In some embodiments, the $^{13}$N-oxytocin peptide formulation or composition comprises between about 0.01 mg/mL and about 12 mg/mL, between about 0.05 mg/mL and about 16 mg/mL, between about 0.1 mg/mL and about 12 mg/mL, between about 0.1 mg/mL and about 8 mg/mL, between about 0.1 mg/mL and about 4 mg/mL, between about 0.1 mg/mL and about 2 mg/mL, between about 0.1 mg/mL and about 1.6 mg/mL, between about 0.1 mg/mL and about 1.2 mg/mL, between about 0.1 mg/mL and about 1 mg/mL, between about 0.1 mg/mL and about 0.8 mg/mL, between about 0.1 mg/mL and about 0.4 mg/mL, between about 0.1 mg/mL and about 0.3 mg/mL, between about 0.2 mg/mL and about 16 mg/mL, between about 0.2 mg/mL and about 12 mg/mL, between about 0.2 mg/mL and about 10 mg/mL, between about 0.2 mg/mL and about 8 mg/mL, between about 0.2 mg/mL and about 6 mg/mL, between about 0.2 mg/mL and about 4 mg/mL, between about 0.2 mg/mL and about 2 mg/mL, between about 0.2 mg/mL and about 1.6 mg/mL, between about 0.2 mg/mL and about 1.2 mg/mL, between about 0.2 mg/mL and about 1 mg/mL, between about 0.2 mg/mL and about 0.8 mg/mL, between about 0.2 mg/mL and about 0.6 mg/mL, between about 0.2 mg/mL and about 0.4 mg/mL, between about 0.2 mg/mL and about 0.3 mg/mL, between about 0.3 mg/mL and about 16 mg/mL, between about 0.3 mg/mL and about 12 mg/mL, between about 0.3 mg/mL and about 10 mg/mL, between about 0.3 mg/mL and about 8 mg/mL, between about 0.3 mg/mL and about 4 mg/mL, between about 0.3 mg/mL and about 3 mg/mL, between about 0.3 mg/mL and about 1 mg/mL, between about 0.3 mg/mL and about 0.5 mg/mL, between about 0.5 mg/mL and about 16 mg/mL, between about 0.5 mg/mL and about 10 mg/mL, between about 0.5 mg/mL and about 5 mg/mL, between about 0.5 mg/mL and about 1 mg/mL, between about 1 mg/mL and about 16 mg/mL, between about 1 mg/mL and about 10 mg/mL, or between about 1 mg/mL and about 5 mg/mL of oxytocin. In some embodiment, the $^{13}$N-oxytocin peptide formulation or composition comprises between about 0.1 mg/mL and about 2 mg/mL, between about 0.15 mg/mL and about 1.5 mg/mL, or between about 0.2 mg/mL and about 1.2 mg/mL of oxytocin. In some embodiments, the $^{13}$N-oxytocin peptide comprises the human oxytocin amino acid sequence consisting of Cys-Tyr-Ile-Gln-Asn-Cys-Pro-Leu-Gly (SEQ ID NO: 1). In some embodiments, the $^{13}$N-oxytocin peptide is the compound of Formula (IV).

In some embodiments, the $^{13}$N-oxytocin peptide formulation or composition is a liquid formulation comprising between about 5 IU/mL and about 8000 IU/mL of oxytocin (including $^{13}$N-oxytocin peptide and non-radiolabeled oxytocin). In some embodiments, the $^{13}$N-oxytocin peptide formulation or composition comprises between about 500 IU/mL and about 6000 IU/mL, between about 25 IU/mL and about 8000 IU/mL, between about 50 IU/mL and about 6000 IU/mL, between about 50 IU/mL and about 4000 IU/mL, between about 50 IU/mL and about 2000 IU/mL, between about 50 IU/mL and about 1000 IU/mL, between about 50 IU/mL and about 800 IU/mL, between about 50 IU/mL and about 600 IU/mL, between about 50 IU/mL and about 500 IU/mL, between about 50 IU/mL and about 400 IU/mL, between about 50 IU/mL and about 200 IU/mL, between about 50 IU/mL and about 150 IU/mL, between about 100 IU/mL and about 8000 IU/mL, between about 100 IU/mL and about 6000 IU/mL, between about 100 IU/mL and about 5000 IU/mL, between about 100 IU/mL and about 4000 IU/mL, between about 100 IU/mL and about 3000 IU/mL, between about 100 IU/mL and about 2000 IU/mL, between about 100 IU/mL and about 1000 IU/mL, between about 100 IU/mL and about 800 IU/mL, between about 100 IU/mL and about 600 IU/mL, between about 100 IU/mL and about 500 IU/mL, between about 100 IU/mL and about 400 IU/mL, between about 100 IU/mL and about 300 IU/mL, between about 100 IU/mL and about 200 IU/mL, between about 100 IU/mL and about 150 IU/mL, between about 150 IU/mL and about 8000 IU/mL, between about 150 IU/mL and about 6000 IU/mL, between about 150 IU/mL and about 5000 IU/mL, between about 150 IU/mL and about 4000 IU/mL, between about 150 IU/mL and about 2000 IU/mL, between about 150 IU/mL and about 1500 IU/mL, between about 150 IU/mL and about 500 IU/mL, between about 150 IU/mL and about 250 IU/mL, between about 250 IU/mL and about 8000 IU/mL, between about 250 IU/mL and about 5000 IU/mL, between about 250 IU/mL and about 2500 IU/mL, between about 250 IU/mL and about 500 IU/mL, between about 500 IU/mL and about 8000 IU/mL, between about 500 IU/mL and about 5000 IU/mL, or between about 500 IU/mL and about 2500 IU/mL of oxytocin. In a preferred embodiment, the $^{13}$N-oxytocin peptide formulation or composition comprises between about 50 IU/mL and about 1000 IU/mL, between about 75 IU/mL and about 750 IU/mL, or between about 100 IU/mL and about 600 IU/mL of oxytocin. In some embodiments, the $^{13}$N-oxytocin peptide comprises the human oxytocin amino acid sequence consisting of Cys-Tyr-Ile-Gln-Asn-Cys-Pro-Leu-Gly (SEQ ID NO: 1). In some embodiments, the $^{13}$N-oxytocin peptide is the compound of Formula (IV).

Any divalent metal cation salt (such as a water-soluble divalent metal cation salt) may be used to provide divalent metal cation (e.g., $Mg^{2+}$, $Ca^{2+}$, $Zn^{2+}$, or $Cu^{2+}$) in a divalent metal cation-containing $^{13}$N-oxytocin peptide formulation of this invention. The divalent metal cation salt used in the divalent metal cation-containing $^{13}$N-oxytocin peptide formulation may be selected based on a number of factors such as the amount of free divalent metal cation ion that can be delivered when the formulation is administered, the solubility of the divalent metal cation salt in the media for a liquid formulation, the acidity/basicity of the counter ion, and/or the dissociation constant of the salt. For example, in a liquid formulation, the divalent metal cation salt needs to be sufficiently soluble in the liquid media to deliver the divalent metal cation ion concentration required for producing synergistic analgesia with the oxytocin peptide. Other factors may also be considered when selecting the divalent metal cation salt, such as compatibility with other substances in the formulation and ability of the counter ion to perform other functions in the formulation. For example, magnesium citrate is sufficiently soluble in an aqueous solution to provide the desirable amount of divalent metal cation or desirable divalent metal cation ion concentration; citrate salts are pharmaceutically acceptable; the citrate can be part of the buffering agents; and magnesium citrate may add a pleasant flavor for the formulation. The divalent metal cations in the divalent metal cation-containing $^{13}$N-oxytocin peptide formulation may be provided by using one or more divalent metal cation salts. A divalent metal cation salt in the divalent metal cation-containing $^{13}$N-oxytocin peptide formulation may be a divalent metal cation salt used initially in preparing of the divalent metal cation-containing $^{13}$N-oxytocin peptide formulation, or formed in situ during preparation of the divalent metal cation-containing $^{13}$N-oxytocin peptide formulation. For example, magnesium chloride may be used initially in preparing the formulation; and upon addition of citric acid to the formulation, magnesium citrate may be formed in situ. In such instance, the divalent metal cations in the divalent metal cation-containing $^{13}$N-oxytocin peptide formulation are provided by both magnesium chloride and magnesium citrate.

The divalent metal cation salt used in the divalent metal cation-containing $^{13}$N-oxytocin peptide formulations described herein can be obtained from commercial sources or prepared following methods known in the art. For example, magnesium citrate may be prepared following procedures described in Staszczuk P, et al. Physicochem Probl Mineral Proc 37: 149-158 (2003), U.S. Pat. Nos. 1,936,364 and 2,260,004).

In some embodiments, the $^{13}$N-oxytocin peptide formulation or composition further comprises one or more pharmaceutically acceptable carriers (thus constituting a pharmaceutical composition) and optionally other ingredients, such as excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Exemplary excipients include solubilizers, surfactants and chelators. For example, formulations may include, methyl-β-cyclodextrin (Me-β-CD), edetate disodium, arginine, sorbitol, NaCl, methylparaben sodium (MP), propylparaben sodium (PP), chlorobutanol (CB), benzyl alcohol, zinc chloride, ethyl alcohol, didecanoyl L-α-phosphatidylcholine (DDPC), polysorbate, lactose, citrate, tartrate, acetate, and/or phosphate.

Liquid carriers include, but are not limited to, water, saline, aqueous dextrose, and glycols particularly (when isotonic) for solutions. The carrier can also be selected from various oils, including those of petroleum, animal, vegetable or synthetic origin (e.g. peanut oil, olive oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, anti-oxidants, chelating agents, wetting agents, emulsifying agents, dispersing agents, jelling agents, salts for adjusting osmotic pressure, buffers, and the like. A liquid carrier may be hypotonic or isotonic with body fluids and may have a pH within the range of 3.5-8.5. The use of additives in the preparation of peptide and/or protein-based compositions, particularly pharmaceutical compositions, is well-known in the art. In some embodiments, the composition has a pH of about 2 to about 7. In some embodiments, the composition has a pH of about 4 to about 7. In a preferred embodiment, the pH of the formulation/composition is about 4.5.

In some embodiments, the $^{13}$N-oxytocin peptide formulation or composition may further comprise one or more mucosal delivery-enhancing agents selected from (A)-(K): (A) solubilization agents; (B) charge modifying agents; (C) pH control agents; (D) degradative enzyme inhibitors; (E) mucolytic or mucus clearing agents; (F) ciliostatic agents; (G) membrane penetration-enhancing agents; (H) modulatory agents of epithelial junction physiology, such as nitric oxide (NO) stimulators, chitosan, and chitosan derivatives; (I) vasodilator agents; (J) selective transport-enhancing agents; and (K) stabilizing delivery vehicles, carriers, supports or complex-forming species with which the $^{13}$N-oxytocin peptide is effectively combined, associated, contained, encapsulated or bound to stabilize the active agent for enhanced mucosal delivery. Membrane penetration-enhancing agents in Group (G) may be (i) a surfactant, (ii) a bile salt, (iii) a phospholipid or fatty acid additive, mixed micelle, liposome, or carrier, (iv) an alcohol, (v) an enamine, (vi) an NO donor compound, (vii) a long-chain amphipathic molecule, (viii) a small hydrophobic penetration enhancer; (ix) sodium or a salicylic acid derivative; (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii). In various embodiments of the invention, an $^{13}$N-oxytocin peptide may be combined with one, two, three, four or more of the mucosal delivery-enhancing agents recited in (A)-(K). These mucosal delivery-enhancing agents may be admixed, alone or together, with the $^{13}$N-oxytocin peptide, or otherwise combined therewith in a pharmaceutically acceptable formulation or delivery vehicle. The $^{13}$N-oxytocin peptide formulation or composition described herein may provide increased bioavailability of the $^{13}$N-oxytocin peptide following delivery thereof to a mucosal surface (e.g., in the nasal cavities) of a mammalian subject.

The lists of carriers and additives discussed herein are by no means complete and a worker skilled in the art can choose carriers and excipients from the GRAS (generally regarded as safe) list of chemicals allowed in pharmaceutical preparations and those that are currently allowed by the U.S. Food and Drug Administration in topical and parenteral formulations, and those that become allowed in the future. (See also Wang et al., (1980) *J. Parent. Drug Assn.,* 34:452-462; Wang et al., (1988) *J Parent. Sci. and Tech.,* 42:S4-S26.)

In some embodiments, the $^{13}$N-oxytocin peptide formulation or composition further comprises one or more solvent or excipient selected from the group consisting of chlorobutanol, benzalkonium, methyl 4-hydroxybenzoate, propyl 4-hydroxybenzoate, acetic acid, citric acid, glycerol, sodium chloride, sodium monohydrogen phosphate, sorbitol and water. In some embodiments, the $^{13}$N-oxytocin peptide formulation or composition further comprises chlorobutanol, acetic acid and water.

In some embodiments, the $^{13}$N-oxytocin peptide formulation or composition further comprises a chitosan-containing excipient (e.g., ChiSys®, http://www.archimedespharma.com/productArchiDevChiSys.html). In some embodiments, the $^{13}$N-oxytocin peptide formulation or composition further comprises about 1% of the chitosan-containing excipient. In some embodiments, a chitosan glutamate salt may be preferred for nasal delivery for its superior absorption enhancing ability. In some embodiments, chitosan co-polymer nanoparticles may be used, such as nanoparticles containing chitosan glutamate and a negatively charged polymer (e.g., tripolyphosphate pentasodium). Thiolated chitosans (e.g. chitosan covalently modified with 2-iminothiolane), which have been used in microparticles containing insulin and reduced glutathione, may also be useful as an excipient in the $^{13}$N-oxytocin peptide formulation or composition described herein.

In some embodiments, the $^{13}$N-oxytocin peptide formulation or composition further comprises one or more gelling agents, such that the $^{13}$N-oxytocin peptide formulation forms a gel in the nasal cavity, thus enhancing nasal absorption of the $^{13}$N-oxytocin peptide. Gelling systems useful in the formulations and methods described herein may include any known gelling system, such as a chemically reactive pectin-based gelling system (e.g., PecSys™, Archimedes Pharma) and a thermoreactive polymer gelling system (e.g., Pluronic® F127, BASF). PecSys™ is a low viscosity aqueous pectin based solution, delivered as a fine mist in which each droplet gels on contact with calcium ions in the nasal mucosa. Other low methoxy pectin could also be employed, e.g., at about 1% concentration. Pluronic® F127 contains ethylene oxide/propylene oxide block copolymers. The gelling temperatures vary depending on the ratios of components and the amount of co-polymer employed in the final formulation. Gelling in the human nasal cavity has been demonstrated for Pluronic® F127 at approximately 18-20% wt/vol, for examples, as used in a vitamin B12 gel supplement (EnerB, Nature's Bounty, NY) and in a gelling sumatriptan, which contains 18% wt/vol Pluronic® F127 and 0.3% wt/vol Carbopol (anionic bioadhesive polymer C934P). The monomer ratios and concentrations may be adjusted for the intended $^{13}$N-oxytocin formulations to ensure gelling at 25-37° C., around the typical temperature of 34° C. in nasal cavity. If the gelation temperature is lower than 25° C., the formulation could gel at room temperature; if the gelation temperature is above 37° C., the formulation would not fully gel on contact with the nasal mucosa. In some embodiments, the $^{13}$N-oxytocin peptide formulation or composition may further comprise a mucoadhesive agent such as Carbopol. Addition of a mucoadhesive, e.g., addition of up to 0.5% Carbopol, may further lower the gelation temperature.

In some embodiments, the $^{13}$N-oxytocin peptide formulation or composition further comprises a surface active agent, such as a nonionic surfactant (e.g., polysorbate-80), and one or more buffers, stabilizers, or tonicifiers. In some embodiments, the $^{13}$N-oxytocin peptide formulation or composition further comprises a propellant. The pH of the nasal spray solution is optionally between about pH 3.0 and 8.5, but when desired the pH is adjusted to optimize delivery of a charged macromolecular species (e.g., a therapeutic protein or peptide) in a substantially unionized state. The pharmaceutical solvents employed can also be a slightly acidic aqueous buffer (pH 3-6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzalkonium chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid (EDTA), and the like. Suitable gases include, but are not limited to, nitrogen, helium, chlorofluorocarbons (CFCs), hydrofluorocarbons (HFCs), carbon dioxide, air, and the like. Suitable stabilizers and tonicifying agents include sugars and other polyols, amino acids, and organic and inorganic salts. In some embodiments, the $^{13}$N-oxytocin peptide formulation or composition further comprises a citrate salt, a succinate salt or a pyrophosphate salt.

To further enhance the mucosal delivery of the $^{13}$N-oxytocin peptide, an enzyme inhibitor, particularly proteases inhibitors, can be included further in the formulation. Protease inhibitors may include, but are not limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH$_2$, DAPT, diprotin A and B, ebelactone A and B, foroxymithine, leupeptin, phosphoramidon, aprotinin, puromycin, BBI, soybean trypsin inhibitor, phenylmethylsulfonyl fluoride, E-64, chymostatin, 1,10-phenanthroline, EDTA and EGTA. Other enzyme inhibitors such as bacitracin may also be included in the formulation.

To enhance delivery into or across a mucosal surface and/or absorption of the $^{13}$N-oxytocin peptide, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Enhancement of mucosal delivery can thus occur by any of a variety of mechanisms, for example by increasing the diffusion, transport, persistence or stability of the $^{13}$N-oxytocin peptide, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive/mucoadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

All peptides described and/or contemplated herein can be prepared by chemical synthesis using either automated or manual solid phase synthetic technologies, generally known in the art. The peptides can also be prepared using molecular recombinant techniques known in the art.

Oxytocin Administration

The $^{13}$N-oxytocin peptide formulation or composition may be adapted for craniofacial mucosal administration (e.g., nasal, buccal, sublingual or ocular administration). In some embodiments, the composition may be adapted for use with a device for mucosal delivery. In some embodiments, the composition is adapted for buccal and/or sublingual mucosal delivery, which may be for use with a device for buccal and/or sublingual mucosal administration, such as unit dose containers, pump sprays, droppers, squeeze bottles, airless and preservative-free sprays, nebulizers, dose inhalers and pressurized dose inhalers. In some embodiments, the composition is adapted for ocular delivery, which may be for use with a device for conjunctival administration, such as a dropper or a squeeze bottle. In some embodiments, the composition is adapted for intranasal administration, which may be for use with a device for intranasal administration, such as a dropper, pump spray, squeeze bottle, airless and preservative-free sprays, or a nasal pump apparatus, e.g., a nasal pump apparatus comprising a reservoir bottle attached to an aerosolizer.

In embodiments where the $^{13}$N-oxytocin peptide formulation or composition is administered intranasally, the composition can be prepared as a liquid aerosol formulation optionally combined with a dispersing agent and/or a physiologically acceptable diluent. Alternatively, dry powder aerosol formulations are contemplated, and may contain a finely divided solid form of the subject compound and a dispersing agent allowing for the ready dispersal of the dry powder particles. With either liquid or dry powder aerosol formulations, the formulation is aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter for nasal or pulmonary distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

In embodiments where the $^{13}$N-oxytocin peptide formulation or composition is administered intranasally, administration is carried out by a device for intranasal delivery. The device may be any device suitable for intranasal administration of the $^{13}$N-oxytocin peptide formulation. In some embodiments, the device is suitable for delivery of the $^{13}$N-oxytocin peptide to a specific region within the nasal cavity. In some embodiments, the device is suitable for delivery of the $^{13}$N-oxytocin peptide to the inferior two-thirds of the nasal cavity. In some embodiments, the device is suitable for delivery of the $^{13}$N-oxytocin peptide to the upper third of the nasal cavity. In some embodiments, the device is suitable for delivery of the $^{13}$N-oxytocin peptide to the entire nasal passage.

In some embodiments, the device for intranasal delivery is a nasal pump apparatus. In some embodiments, the nasal pump apparatus comprises a reservoir bottle attached to a pump actuator. In some embodiments, the pump actuator is metered to deliver a specified volume (e.g. about 50 to about 150 µL, preferably about 50 µL or about 100 µL) in a specified distribution of droplet sizes. In some embodiments, the nasal pump apparatus comprises a reservoir bottle attached to an aerosolizer, e.g. an Equadel pump marketed by Aptar Pharma. In some embodiments, the device for nasal administration functions irrespective of the pressure applied to the pump once a threshold value is reached. For administration in large mammals, the nasal pump apparatus may comprise a reservoir bottle attached to a pump actuator that is metered to deliver larger volumes (e.g., about 100 µL to about 600 µL, or higher).

In some embodiments, the device for intranasal delivery is designed for delivery of multiple doses of the drug formulations. For example, a nasal pump apparatus may comprise a reservoir bottle attached to a pump actuator where the reservoir bottle holds multiple dose of the liquid formulation and the pump actuator is metered to deliver a specified volume that is a fraction of the liquid formulation held in the reservoir bottle. In some embodiments, the pump actuator is metered to deliver about 50 µL of the liquid formulation per spray. The nasal pump apparatus may comprise a filter for preventing back flow in order to reduce contaminant (e.g., bacterial) ingress into the reservoir bottle. In some embodiments, the nasal pump apparatus comprises a metal-free path for delivery of the liquid formulation (e.g., a plastic path). In some embodiments, the pump apparatus uses plastic material that is stable to gamma radiation (used for sterilizing the nasal apparatus). In some embodiments, the device for intranasal delivery is equipped with a multi-dose pump comprising a microbial filter and an auto-blocking mechanism in the pump actuator, for example, a spray device described in U.S. Pat. No. 5,988,449.

In some embodiments, the device for intranasal delivery is a breath-actuated nasal delivery device, such as the devices described in U.S. Pat. Nos. 7,784,460 and 7,854,227. Such devices may improve delivery to a target site deep into the nasal cavity. In some embodiments, a standard metered dose spray device is incorporated into a housing that allows the patient to blow into a mouthpiece to actuate the device. In some embodiments, the device is comprised of a conical sealing nosepiece and a mouthpiece that incorporate a traditional mechanical spray pump (e.g. an Equadel pump marketed by Aptar Pharma), a chargeable spring and a breath actuation mechanism. The system can be used for single or multi-dose delivery. One example of such a liquid delivery device is the OptiMist™ device marketed by Opti-Nose. When in use, the nasal piece of the device is inserted into the nostril and the mouth piece is blown into. This closes the soft palate, transfers pressure to the nostril, opens passages providing airflow behind the nasal septum and allows air to exit the other nostril (bidirectional flow). Since the device is breath actuated, small particles cannot enter the lungs. Modifications to flow rate and particle size allows for targeting of specific nasal regions.

In some embodiments, the device for intranasal delivery is a unit-dose metering spray device suited for single administration of the $^{13}$N-oxytocin peptide formulation or composition. In some embodiments, the device for intranasal delivery is a multi-dose metering spray pump apparatus suited for repeated administrations of an $^{13}$N-oxytocin peptide.

Drop size, plume volume and flow rate can be modified to target specific nasal regions. The liquid spray may provide droplet size between 5 and 50 microns in order to target olfactory and/or respiratory epithelium. Larger droplets primarily travel down the nasopharynx and are swallowed, while smaller droplets are targeted to the pulmonary tissue. The Mass Median Equivalent Aerodynamic Diameter (MMAD) is used to specify the drop size. The pH of the nasal spray is optimized to deliver charged peptide in mostly an unionized state. The nose will generally tolerate solutions having a pH of about 3-8. The nasal mucosa can generally absorb volumes of approximately 100 µL before saturation occurs and liquid begins to drip out of the nose. Therefore, plume volume may be up to (and including) 100 µL. For use in large mammals, plume volume may be up to (and including) 150 µL or higher (e.g., 600 µL or higher). For infant and pediatric use, or for veterinary use in smaller animals (e.g., rodents, cats), smaller plume volumes (5-50 µL) could be used.

In some embodiments, the device for intranasal delivery is ergonomically designed to facilitate patient compliance, such as a pump apparatus with a side-actuation triggering mechanism. In some embodiments, the device for intranasal delivery comprises a metering spray pump working as a closed system, which does not allow air to enter into the pump apparatus thus preventing contamination from airborne germs. In some embodiment, the device for intranasal delivery comprises a metering spray pump working with a filter. The venting air is sucked through a filter assembled inside the pump, keeping airborne germs out of the pump apparatus. In some embodiments, the intranasal delivery device comprising a nasal pump apparatus may further comprise micro-electronic devices that may facilitate data transmission and treatment monitoring.

In some embodiments, the $^{13}$N-oxytocin peptide formulation or composition comprises an $^{13}$N-oxytocin peptide, wherein the $^{13}$N-oxytocin peptide is contained in any one of the devices for intranasal delivery described herein, and wherein the concentrations of oxytocin (including $^{13}$N-oxytocin and non-radiolabeled oxytocin) in the $^{13}$N-oxytocin peptide formulation or composition are within any of the concentration ranges described herein, as if each and every combination of device and concentration is described individually. In some embodiments, the $^{13}$N-oxytocin peptide formulation or composition comprises an $^{13}$N-oxytocin peptide and non-radiolabeled oxytocin. In some embodiments, the amount of $^{13}$N-oxytocin peptide in the $^{13}$N-oxytocin peptide formulation or composition is in the range of about 0.05 μg/mL to about 5 μg/mL (such as about any of 0.05, 0.1, 0.2, 0.3, 0.4, 0.5, 0.6, 0.7, 0.8, 0.9, 1, 2, 3, 4, or 5 μg/mL, including any ranges between these values).

In some embodiments, the $^{13}$N-oxytocin peptide is administered concurrently or sequentially with another agent. In some embodiments, the other agent is non-radiolabeled oxytocin. In some embodiments, the other agent affects the distribution, kinetics, and/or pharmacodynamics of oxytocin. In some embodiments, the other agent is a divalent metal cation (e.g., $Mg^{2+}$, $Ca^{2+}$, $Zn^{2+}$, or $Cu^{2+}$). In some embodiments, the divalent metal cation is $Mg^{2+}$. In some embodiments, the other agent is vasopressin. In some embodiments, the $^{13}$N-oxytocin peptide is administered concurrently with the other agent in the same unit dose. In some embodiments, the $^{13}$N-oxytocin peptide is administered concurrently with the other agent but in separate unit doses or formulations. In some embodiments, $^{13}$N-oxytocin peptide and the other agent are administered sequentially. In some embodiments, the other agent is administered to the subject in a first administration and then the $^{13}$N-oxytocin peptide is administered to the subject in a second administration. In some of these embodiments, the $^{13}$N-oxytocin peptide is administered between about 10 minutes and about 2 hours after administration of the other agent. In some of these embodiments, the $^{13}$N-oxytocin peptide is administered between about 10 minutes and about 2 hours, between about 10 minutes and about 1 hour, between about 10 minutes and about 30 minutes, between about 20 minutes and about 2 hours, between about 20 minutes and about 1 hour, between about 30 minutes and about 2 hours or between about 30 minutes and about 1 hour after administration of the other agent. In some of these embodiments, the $^{13}$N-oxytocin peptide is administered about 10 minutes, about 15 minutes, about 20 minutes, about 30 minutes, about 45 minutes, about 60 minutes, about 90 minutes or about 120 minutes after administration of the other agent. In some of these embodiments, the $^{13}$N-oxytocin peptide is administered about 10 minutes, about 15 minutes, about 20 minutes, about 30 minutes after administration of the other agent. In one embodiment, the $^{13}$N-oxytocin peptide is administered to the subject first and then the other agent is administered to the subject. In some embodiments, the subject is a human.

In some embodiments, the $^{13}$N-oxytocin peptide and the other agent may be administered via the same route or different routes to a subject in need thereof. In some embodiments, the $^{13}$N-oxytocin peptide is administered via craniofacial mucosal administration (e.g., nasal, buccal, sublingual or ocular administration). In one embodiment, the $^{13}$N-oxytocin peptide and the other agent are both administered intranasally in the same formulation. In one embodiment, the $^{13}$N-oxytocin peptide is administered via craniofacial mucosa and the other agent is administered systemically, e.g., intravenously, intramuscularly, orally, subcutaneously, or intrathecally.

In some embodiments, the $^{13}$N-oxytocin peptide is administered via intranasal administration. In some embodiments, the $^{13}$N-oxytocin peptide and the other agent are administered via intranasal administration. The $^{13}$N-oxytocin peptide and/or the other agent can be administered to the mucosa tissue within the nasal cavity using a suitable device for intranasal delivery such as a nasal delivery device described herein. Suitable regions within the nasal cavity include, but are not limited to, the inferior two-thirds of the nasal cavity, or the upper third, or the entire nasal passage. In some embodiments, the $^{13}$N-oxytocin peptide and/or the other agent are administered to the upper third of the nasal cavity. In some embodiments, the $^{13}$N-oxytocin peptide and/or the other agent are administered to the lower two thirds of the nasal cavity. In some embodiments, the $^{13}$N-oxytocin peptide and/or the other agent are administered specifically to reach both the lower two thirds and the upper third of the nasal cavity.

In some embodiments, the $^{13}$N-oxytocin peptide comprises the human oxytocin amino acid sequence consisting of Cys-Tyr-Ile-Gln-Asn-Cys-Pro-Leu-Gly (SEQ ID NO: 1). In some embodiments, the $^{13}$N-oxytocin peptide is the compound of Formula (IV). In some embodiments, an effective dose of an $^{13}$N-oxytocin peptide formulation or composition comprises oxytocin (including $^{13}$N-oxytocin and non-radiolabeled oxytocin) in a range of about 0.5 μg to about 2000 μg. In some embodiments, the effective dose of oxytocin in an $^{13}$N-oxytocin peptide formulation or composition is about 0.5 μg to about 1000 μg, about 1 μg to about 1000 μg or about 1 μg to about 2000 μg. In some embodiments, the effective dose of oxytocin in an $^{13}$N-oxytocin peptide formulation or composition is about 4 μg to about 1000 μg, about 8 μg to about 1000 μg, about 8 μg to about 800 μg, about 8 μg to about 500 μg, about 8 μg to about 400 μg, about 8 μg to about 300 μg, about 8 μg to about 200 μg, about 8 μg to about 100 μg, about 8 μg to about 80 μg, about 8 μg to about 50 μg, about 10 μg to about 1000 μg, about 10 μg to about 500 μg, about 10 μg to about 200 μg, about 10 μg to about 100 μg, about 16 μg to about 1000 μg, about 16 μg to about 800 μg, about 16 μg to about 500 μg, about 16 μg to about 400 μg, about 16 μg to about 200 μg, about 16 μg to about 160 μg, about 16 μg to about 120 μg, about 16 μg to about 80 μg, about 20 μg to about 1000 μg, about 20 μg to about 800 μg, about 20 μg to about 500 μg, about 20 μg to about 200 μg, about 20 μg to about 100 μg, about 30 μg to about 1000 μg, about 30 μg to about 500 μg, about 30 μg to about 300 μg, about 30 μg to about 120 μg, about 30 μg to about 90 μg, about 50 μg to about 1000 μg, about 50 μg to about 500 μg, about 50 μg to about 250 μg, about 50 μg to about 100 μg, or about 50 μg to about 80 μg. In some embodiments, the effective dose of oxytocin in an $^{13}$N-oxytocin peptide formulation or composition is about 8 μg, about 16 μg, about 32 μg, about 48 μg, about 64 μg, about 80 μg, about 96 μg, about 128 μg, about 256 μg, about 10 μg, about 20 μg, about 30 μg, about 40 μg, about 50 μg, about 60 μg, about 70 μg, about 80 μg, about 90 μg, about 100 μg, about 120 μg, about 150 μg, about 200 μg, about 400 μg, about 600 μg, about 800 μg or about 100 μg. In some embodiments, the effective dose of oxytocin in an $^{13}$N-oxytocin peptide formulation or composition is about 8 μg to about 120 μg, about 15 μg to about 120 μg, about 30 μg to about 120 μg, or about 66 μg. In some embodiments, the amount of $^{13}$N-oxytocin peptide in an effective dose of an $^{13}$N-oxytocin peptide formulation or composition is in the range of about $1\times10^{-4}$ μg to about $1\times10^{-2}$ g (such as about any of $1\times10^{-4}$, $5\times10^{-3}$, $1\times10^{-3}$, $5\times10^{-2}$, or $1\times10^{-2}$ g, including any ranges between these values).

In some embodiments, the effective dose of oxytocin (including $^{13}$N-oxytocin and non-radiolabeled oxytocin) in an $^{13}$N-oxytocin peptide formulation or composition is about 0.25 IU to about 1000 IU. In some embodiments, the effective dose of oxytocin in an $^{13}$N-oxytocin peptide formulation or composition is about 0.25 IU to about 500 IU, about 0.5 IU to about 500 IU or about 0.5 IU to about 1000 IU. In some embodiments, the effective dose of oxytocin in an $^{13}$N-oxytocin peptide formulation or composition is about 2 IU to about 500 IU, about 4 IU to about 500 IU, about 4 IU to about 400 IU, about 4 IU to about 250 IU, about 4 IU to about 200 IU, about 4 IU to about 150 IU, about 4 IU to about 100 IU, about 4 IU to about 50 IU, about 4 IU to about 40 IU, about 4 IU to about 25 IU, about 5 IU to about 500 IU, about 5 IU to about 250 IU, about 5 IU to about 100 IU, about 5 IU to about 50 IU, about 8 IU to about 500 IU, about 8 IU to about 400 IU, about 8 IU to about 250 IU, about 8 IU to about 200 IU, about 8 IU to about 100 IU, about 8 IU to about 80 IU, about 8 IU to about 60 IU, about 8 IU to about 40 IU, about 10 IU to about 500 IU, about 10 IU to about 400 IU, about 10 IU to about 250 IU, about 10 IU to about 100 IU, about 10 IU to about 50 IU, about 15 IU to about 500 IU, about 15 IU to about 250 IU, about 15 IU to about 150 IU, about 15 IU to about 60 IU, about 15 IU to about 45 IU, about 25 IU to about 500 IU, about 25 IU to about 250 IU, about 25 IU to about 125 IU, about 25 IU to about 50 IU, or about 25 IU to about 40 IU. In some embodiments, the effective dose of oxytocin in an $^{13}$N-oxytocin peptide formulation or composition is about 4 IU, about 8 IU, about 16 IU, about 24 IU, about 32 IU, about 40 IU, about 48 IU, about 64 IU, about 128 IU, about 5 IU, about 10 IU, about 15 IU, about 20 IU, about 25 IU, about 30 IU, about 35 IU, about 40 IU, about 45 IU, about 50 IU, about 60 IU, about 75 IU, about 100 IU, about 200 IU, about 300 IU, about 400 IU or about 50 IU. In some embodiments, the effective dose of oxytocin in an $^{13}$N-oxytocin peptide formulation or composition is about 4 IU to about 60 IU, about 7.5 IU to about 60 IU, about 15 IU to about 60 IU, or about 30 IU.

Kits

Provided herein are kits for carrying out any of the methods described herein. Kits are provided for use in the administration of $^{13}$N-oxytocin to an individual (such as craniofacial mucosal administration, e.g., intranasal administration). In some embodiments, the kit comprises an $^{13}$N-oxytocin peptide, such as a peptide according to Formula (IV). In some embodiments, the kit comprises an $^{13}$N-oxytocin peptide precursor for use in the synthesis of an $^{13}$N-oxytocin peptide, such as a peptide according to Formulas (I), (Ia), (Ib), (II), (IIa), and/or (IIb). In some embodiments, the kit comprises reagents for use in the synthesis of an $^{13}$N-oxytocin peptide from a precursor, including DECP, PMP, DMSO, THF, HCl, and/or dioxane. In some embodiments, the kit comprises reagents and/or articles of manufacture for the purification of an $^{13}$N-oxytocin peptide, including SPE columns (e.g., C18 sep-pak) and/or ion-pairing reagents. In some embodiments, the kit comprises a device for craniofacial mucosal administration (e.g., intranasal administration) in suitable packaging. Kits may further comprise any of the oxytocin peptide formulation components described herein, including a protease inhibitor and/or at least one absorption enhancer. Other kits may further comprise instructions providing information to the user and/or health care provider for carrying out any one of the methods described herein.

Also provided is a kit comprising an $^{13}$N-oxytocin peptide formulation described herein contained in a device for craniofacial mucosal administration (e.g., a device for intranasal administration such as a nasal pump apparatus) and suitable packaging. The kit may further comprise instructions for administering the $^{13}$N-oxytocin peptide formulation in a subject.

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

Exemplary Embodiments

Embodiment 1. An $^{13}$N-labeled oxytocin peptide comprising the amino acid sequence of SEQ ID NO: 1.

Embodiment 2. The $^{13}$N-labeled oxytocin peptide of embodiment 1, wherein one component $^{14}$N atom of the oxytocin peptide is replaced by an $^{13}$N radionuclide.

Embodiment 3. The $^{13}$N-labeled oxytocin peptide of embodiment 1 or 2, wherein one residue of the oxytocin peptide is modified to comprise a moiety comprising an $^{13}$N radionuclide.

Embodiment 4. The $^{13}$N-labeled oxytocin peptide of embodiment 3, wherein one residue of the oxytocin peptide is modified to comprise $^{13}$NH$_2$.

Embodiment 5. The $^{13}$N-labeled oxytocin peptide of any one of embodiments 1-4, wherein the $^{13}$N-labeled oxytocin peptide comprises a single $^{13}$N radionuclide.

Embodiment 6. The $^{13}$N-labeled oxytocin peptide of any one of embodiments 1-5, wherein the $^{13}$N-labeled oxytocin peptide comprises an $^{13}$N radionuclide at a) the glutamine residue at position 4 (SEQ ID NO: 2); b) the asparagine residue at position 5 (SEQ ID NO: 3); or c) the glycine residue at position 9 (SEQ ID NO: 4).

Embodiment 7. The $^{13}$N-labeled oxytocin peptide of embodiment 1, wherein the $^{13}$N-labeled oxytocin peptide is the compound of Formula (IV).

Embodiment 8. A method of manufacturing a $^{13}$N-labeled oxytocin peptide comprising the amino acid sequence of SEQ ID NO: 1, the method comprising: a) reacting the compound of Formula (Ib) with diethyl cyanophosphonate (DECP) to provide the compound of Formula (IIb); b) reacting the compound of Formula (IIb) with gaseous $^{13}$NH$_3$ to provide the compound of Formula (IIIb); and c) deprotecting the compound of Formula (IIIb) to provide the $^{13}$N-labeled oxytocin peptide, wherein the $^{13}$N-labeled oxytocin peptide is the compound of Formula (IV).

Embodiment 9. The method of embodiment 8, wherein reacting the compound of Formula (Ib) with DECP is carried out in the presence of dimethyl sulfoxide (DMSO), tetrahydrofuran (THF), and pentamethylpiperidine (PMP).

Embodiment 10. The method of embodiment 8 or 9, wherein the amount of DECP is between about 0.7 and about 1.1 equivalents.

Embodiment 11. The method of embodiment 9 or 10, wherein the ratio of DMSO to THF is between about 1:7 and about 1:11.

Embodiment 12. The method of any one of embodiments 8-11, wherein the deprotecting comprises reacting the compound of Formula (IIIb) with HCl/dioxane.

Embodiment 13. The method of any one of embodiments 8-12, further comprising purifying the $^{13}$N-labeled oxytocin peptide provided in step c) to remove reagents, organic solvents, and precursor.

Embodiment 14. The method of embodiment 13, wherein the purifying comprises purification by solid-phase extraction (SPE).

Embodiment 15. The method of embodiment 14, wherein purification by SPE comprises: a) applying the $^{13}$N-labeled oxytocin peptide to a first hydrophobic SPE column, such that the $^{13}$N-oxytocin and precursor are retained on the first hydrophobic SPE column; b) applying a solution comprising an aqueous ion-pairing reagent to the first hydrophobic SPE column, such that the $^{13}$N-oxytocin is eluted in a first eluate; c) applying the first eluate to a second hydrophobic SPE column, such that the $^{13}$N-oxytocin of the first eluate is retained on the second hydrophobic SPE column; and d) eluting the $^{13}$N-oxytocin in a second eluate.

Embodiment 16. The method of embodiment 15, wherein the first and/or second hydrophobic SPE columns comprise a silica-based bonded phase with strong hydrophobicity.

Embodiment 17. The method of embodiment 15 or 16, wherein the solution comprising an aqueous ion-pairing reagent comprises between about 15% and about 25% acetonitrile.

Embodiment 18. An $^{13}$N-labeled oxytocin peptide prepared by a process comprising the method of any one of embodiments 8-17.

Embodiment 19. A method of determining the distribution of exogenously administered oxytocin in an individual, comprising: a) administering to the individual the $^{13}$N-labeled oxytocin peptide of any one of embodiments 1-8 and 18; b) allowing the $^{13}$N-labeled oxytocin peptide to accumulate at a tissue or cell site to be imaged; and c) imaging the cells or tissues with a non-invasive imaging technique.

Embodiment 20. A method of determining the distribution of oxytocin receptors in an individual, comprising: a) administering to the individual the $^{13}$N-labeled oxytocin peptide of any one of embodiments 1-8 and 18; b) allowing the $^{13}$N-labeled oxytocin peptide to bind to oxytocin receptors; and c) imaging the $^{13}$N-labeled oxytocin peptide in the individual with a non-invasive imaging technique.

Embodiment 21. A method of determining the kinetics of exogenously administered oxytocin in an individual, comprising: a) administering to the individual the $^{13}$N-labeled oxytocin peptide of any one of embodiments 1-8 and 18; and b) imaging the $^{13}$N-labeled oxytocin peptide in the individual over a period of time with a non-invasive imaging technique.

Embodiment 22. The method of any one of embodiments 19-21, wherein the non-invasive imaging technique comprises positron emission tomography imaging.

Embodiment 23. The method of embodiment 22, wherein the non-invasive imaging technique comprises positron emission tomography with computed tomography imaging or positron emission tomography with magnetic resonance imaging.

Embodiment 24. The method of any one of embodiments 19-23, wherein the $^{13}$N-labeled oxytocin peptide is administered via craniofacial mucosal administration.

Embodiment 25. The method of embodiment 24, wherein the $^{13}$N-labeled oxytocin peptide is administered intranasally.

Embodiment 26. The method of any one of embodiments 19-23, wherein the $^{13}$N-labeled oxytocin peptide is administered intravenously, intraarterially, intraperitoneally, intravesicularly, subcutaneously, intrathecally, intrapulmonarily, intramuscularly, intratracheally, ocularly, transdermally, or by suppository.

Embodiment 27. The method of embodiment 26, wherein the $^{13}$N-labeled oxytocin peptide is administered intravenously.

Embodiment 28. A kit comprising the $^{13}$N-labeled oxytocin peptide of any one of embodiments 1-7 and 18.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1: Distribution of Oxytocin Following IV Administration in Rats

Anesthetised rats are scanned using a microPET scanner (nanoscan microPET/1T MRI, Mediso Ltd, Budapest, Hungary). Body temperature is maintained and circulation and respiration are monitored. First, a structural T2-weighted MRI scan is obtained for attenuation correction. Subsequently, the rat is injected through the tail vein with the $^{13}$N-oxytocin radiotracer. A list-mode protocol is used with a 60-min acquisition time. The list-mode data of the emission scans are split into a dynamic sequence of frames. The data are reconstructed per time frame employing an iterative reconstruction. Appropriate correction factors are applied producing quantitative dynamic images (matrix size (x, y, z) 93, 93, 120. Voxel size 0.4 mm. 3D Tera-Tomo reconstruction with Monte Carlo based estimation, attenuation and scatter correction). A summed PET image of each 60 min scan is co-registered to an average Sprague-Dawley rat MRI brain atlas using PMOD software (version 3.7, PMOD Technologies Ltd, Zurich, Switzerland), a commercially available software package for biomedical image quantification, to acquire data in regions of interest. The results are expressed as dimensionless standardized uptake values (SUVs): [tissue activity concentration (MBq/g)×body weight (g)/injected dose (MBq)].

In one study, female Sprague Dawley rats were housed two per cage under a 12 h light/12 h dark cycle at an average temperature of 21° C. and humidity of 55%, with ad libitum access to food and water. The animal experiments were conducted under humane conditions with ethical approval and in accordance with guidelines established by the Danish Animal Experiments Inspectorate (AEI).

Figure 2:
FIG. 2 shows PET and MR scans of a rat following IV administration of oxytocin showing lack of CNS penetration.

A female Sprague Dawley rat (weight: 358 g) was anesthetized in a chamber filled with 2% isoflurane and maintained during dynamic PET acquisition through a mask for delivery of isoflurane (1.5-2%). Temperature, heart rate and respiration frequency were monitored throughout the study. The anesthetized animal was scanned using a microPET scanner (nanoScan® microPET/1T MRI system, Mediso Ltd, Hungary, Budapest) (MRI image resolution 100 μm) by placing the anime prone in the microPET aperture. The head was immobilized in a holder to minimise head movement. First, a structural T2-weighted MRI scan was obtained for attenuation correction. Subsequently, the rat was injected with 13.3 MBq $^{13}$N-oxytocin radiotracer in the tail vein and the PET scan was started. Data was acquired in PET listmode and were reconstructed as 20 frames (30 min (8×15 sec, 8×60 sec, 4×5 min)) with a 3D iterative algorithm (Tera-Tomo 3D, full detector model and normal regularization (Mediso, Budapest, Hungary) with 4 iterations and 6 subsets, and a voxel size of 0.4×0.4×0.4 mm3 (0.064 mm³). Data were corrected for dead-time and decay, and for randoms using delayed coincidence window. Images were corrected for attenuation and scatter using an 18 min long MR GRE EXT sequence (1 excitation, TR 2.0 ms, TE 2.1 ms, flip angle 25°, 0.5 mm slice thickness, horizontal orientation). Upon inspection of the acquired data, no brain uptake of $^{13}$N-oxytocin was noted (FIG. 2).

Example 2: Distribution of Oxytocin Following Nasal Administration in Rats

The distribution of $^{13}$N-oxytocin following nasal administration in rats is tested. Aqueous formulations containing $^{13}$N-oxytocin according to any of the formulations described herein are applied nasally in rats and the distribution of $^{13}$N-oxytocin in the rats is determined by scanning as described above.

Figure 3:
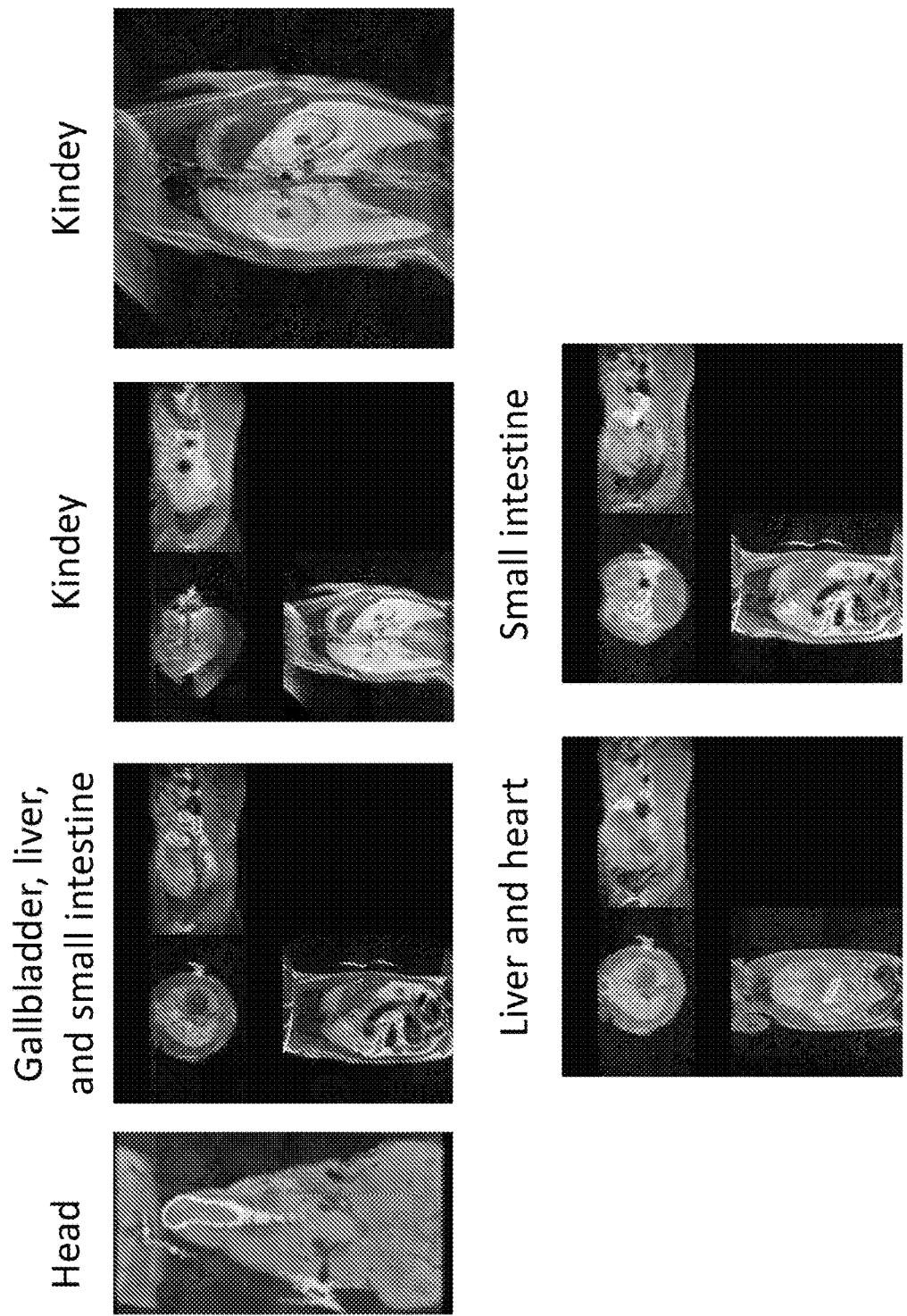
FIG. 3 shows overlays of PET and MR scans of a rat following intranasal administration of oxytocin showing lack of CNS penetration.

In one study, the distribution of $^{13}$N-oxytocin following nasal administration in 2 rats (weighing 257 g and 260 g) was investigated. For each rat, approximately 100 µl of $^{13}$N-oxytocin (dissolved in 10% ethanol/90% saline) solution (around 1-2 MBq) was placed in each nostril by a pipette, and the rat was immediately transferred to the PET scan bed after which a 60 min PET scan started according to the method described in Example 1, followed by a magnetic resonance (MR) scan. As shown in FIG. 3, the tracer $^{13}$N-oxytocin distributed mainly to gallbladder, kidneys and intestine, with no visible brain uptake.

Example 3: Distribution and Kinetics of Oxytocin Following Nasal Administration in Normal Human Subjects The distribution and kinetics of $^{13}$N-oxytocin following nasal administration in normal human subjects is tested. Healthy volunteers are selected based on inclusion/exclusion criteria, history and physical exam, laboratory tests, and other customary procedures. The $^{13}$N-oxytocin is delivered intranasally to the subjects by a metered dose nebulizer. For example, a dose of 0.01 µg/kg of $^{13}$N-oxytocin in 0.1 ml of saline is administered with each nasal puff application to the subjects. 0.1 ml of saline only with each nasal puff application is administered to control subjects. Any of the $^{13}$N-oxytocin formulations described herein can be tested. The $^{13}$N-oxytocin is imaged in the individual over time by PET to determine the distribution and kinetics of the $^{13}$N-oxytocin. In this example, a structural CT or MRI is first performed for accurate anatomical identification. Thereafter the $^{13}$N-oxytocin is administered to the subject, followed by a nasal rinse to allow for an accurate determination of the timing of the oxytocin pulse. A 60 min PET scan starts as soon as the healthy volunteer, migraine patient, or neuropsychiatric patient is properly placed in the PET scanner (Siemens Biograph 64 Truepoint PET). PET data are reconstructed using TrueX 3D OSEM (3 iterations, 21 subsets), a 256×256×109 matrix, and a 2-mm Gauss filter, using a time-frame structure of 5×60, 3×300, 4×600 seconds (total 12 frames, 60 minutes). Preprocessing steps are performed using PMOD 3.7 (PMOD Technologies Ltd, Zurich, Switzerland), a commercially available software package for biomedical image quantification. Dynamic PET acquisitions are visually inspected and motion artifacts are corrected. In all six participants, whole-body emission scans are performed. Safety tests, blood, urine, vital signs, and electrocardiography are obtained before injection and between 120 and 150 min post-injection.

On the whole-body images, ROIs are placed over major organs (brain, lungs, mediastinum, liver, spleen, gallbladder, kidneys, bladder, and ureter). The activity in each source organ and the remainders are divided by the injection activity to obtain the uptake as a percent of the injected activity. The residence time of each source organ is calculated from the percent injection activity of each source organ and the time course information by fitting to an exponential curve using OLINDA 1.0/EXM software (Vanderbilt University). Dosimetry is determined by entering the average residence time of each source organ into OLINDA 1.0/EXM software using the adult male phantom.

Example 4: Distribution, Kinetics, and Pharmacodynamics of Oxytocin Following Nasal Administration in Human Normal Volunteers, Neuropsychiatric Patients, or Chronic Migraineurs Human subjects (normal volunteers, patients suffering from migraine with or without aura, or neuropsychiatric patients) are enrolled. Eligibility for the study is determined by telephone interview and during a first visit at the study center. During the first visit of potential participants at the study center a medical history is taken and a medical exam is performed. In particular, the diagnosis of neuropychiatric illness (e.g., autism spectrum disorder or anxiety disorder), chronic or high frequency episodic migraine headache with or without aura is established by one skilled in the art. If participants meet inclusion criteria and no exclusion criteria apply written informed consent is obtained. Demographic and medical data are recorded.

The pain assessment tool to be used in the migraineurs is a VRS-4. This tool is self-reported and requires subjects to rate their pain level on a 4-category scale (severe, moderate, mild, none). Subjects use a secure mobile ePRO device to enter their pain scores. Subjects are trained on completing the VRS-4, using the mobile device, during their screening visit.

To neuropsychiatric patients, appropriate survey assessments will be used, such as the Autism Diagnostic Observation Scale, the Clinical Global Impression-Improvement (CGI-I) assessment, and/or the Hamilton Anxiety Rating Scale.

The efficacy of the oxytocin formulation is assessed by comparing post-dosing effects on the appropriate measurement tool when compared to pre-treatment as well as the time to onset of effects and the duration of effects.

Subjects are first subjected to a structural MRI or CT scan. Thereafter, subjects are periodically nasally administered the oxytocin peptide formulation, where the oxytocin contains $^{13}$N-oxytocin as well as unlabeled oxytocin. Following administration of the $^{13}$N-oxytocin peptide formulation, the subjects are imaged by PET to determine kinetics and distribution of the $^{13}$N-oxytocin. PET images are analyzed to determine dosimetry and pharmacokinetics and the relationship of these measures to pharmacodynamics (in terms of efficacy). Scanning and analysis is carried out as described above.

Example 5: Method of Synthesizing $^{13}$N-Oxytocin

The following example describes a method of synthesizing the $^{13}$N-oxytocin compound of Formula (IV), comprising a carboxy-terminal $^{13}$NH$_2$, using the compound of Formula (Ib) as a starting reagent. The compound of Formula (Ib) was incubated in a reaction vial with 0.9 equivalents DECP in the presence of dimethyl sulfoxide (DMSO)- tetrahydrofuran (THF) (ratio of 1:9, respectively) containing pentamethylpiperidine (PMP) at room temperature to form the compound of Formula (IIb). $^{13}NH_3$ was produced in a cyclotron by proton irradiation of liquid target ($[^{16}O$ (p, α)$^{13}N]$), and transferred to a glass vial containing NaOH neat through Teflon tubing with helium flow. The released gaseous $^{13}N H_3$ was transferred to the reaction vial containing the compound of Formula (IIb) manually by positive pressure generated by means of a syringe at room temperature to yield the N-Boc-protected compound of Formula (IIIb). The N-Boc-protected compound of Formula (IIIb) was de-protected using 4M HCl/dioxane at 50° C. for 2.5 minutes to yield a crude preparation of the $^{13}N$-oxytocin compound of Formula (IV).

The crude preparation of the $^{13}N$-oxytocin compound of Formula (IV) was purified to remove reagents, organic solvents, and precursor using a multi-step solid-phase extraction (SPE) protocol. In the first step, diluted crude preparation of the $^{13}N$-oxytocin compound of Formula (IV) was applied to a C18 Sep-pak cartridge, allowing the organic solvents and reagents to flow through in the eluate while the $^{13}N$-oxytocin and precursor were retained in the cartridge. In the second step, the $^{13}N$-oxytocin was eluted from the cartridge by applying a 20% solution of acetonitrile comprising an aqueous ion-pairing reagent, and the eluate containing the $^{13}N$-oxytocin was collected. This eluate was diluted and applied to a second C18 Sep-pak cartridge, followed by washing with $H_2O$ to remove the acetonitrile and ion-pairing reagent. Finally, the $^{13}N$-oxytocin was eluted from the cartridge with EtOH, and the eluate containing purified $^{13}N$-oxytocin was collected.

SEQUENCE LISTING

| SEQ ID | Sequence | Annotations |
|---|---|---|
| 1 | CYIQNCPLG | Oxytocin |
| 2 | CYIQNCPLG $^{13}N$-label at Q4 | Q4-$^{13}N$-oxytocin |
| 3 | CYIQNCPLG $^{13}N$-label at N5 | N5-$^{13}N$-oxytocin |
| 4 | CYIQNCPLG $^{13}N$-label at G9 | G9-$^{13}N$-oxytocin |

We claim:

1. An oxytocin peptide comprising the amino acid sequence of CYIQNCPLG (SEQ ID NO: 1), wherein an N atom in an amino acid residue of said oxytocin peptide is replaced by an $^{13}$N radionuclide.

2. The oxytocin peptide of claim 1, wherein the $^{13}$N radionuclide is part of an NH$_2$ moiety.

3. The oxytocin peptide of claim 1, wherein the amino acid residue in which the N atom is modified is selected from the group consisting of the glutamine at position 4, the asparagine at position 5, and the glycine at position 9.

4. The oxytocin peptide of claim 3, wherein the amino acid residue is the glycine at position 9, and wherein the oxytocin peptide has a structure of Formula (IV):

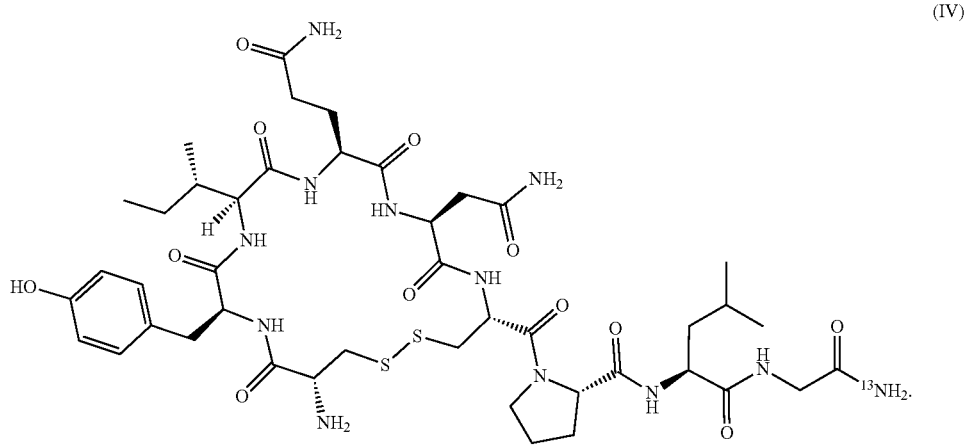

(IV)

5. A kit comprising the oxytocin peptide of claim 1.

* * * * *

UNITED STATES PATENT AND TRADEMARK OFFICE
CERTIFICATE OF CORRECTION

Page 1 of 1

PATENT NO. : 11,970,554 B2
APPLICATION NO. : 16/976912
DATED : April 30, 2024
INVENTOR(S) : Jakobsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Eighth Day of October, 2024

Katherine Kelly Vidal
*Director of the United States Patent and Trademark Office*

```
SEQUENCE LISTING

<160> NUMBER OF SEQ ID NOS: 4

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Labeled with 13N radionuclide

<400> SEQUENCE: 2

Cys Tyr Ile Gln Asn Cys Pro Leu Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Labeled with 13N radionuclide

<400> SEQUENCE: 3

Cys Tyr Ile Gln Asn Cys Pro Leu Gly
1               5

<210> SEQ ID NO 4
```

```
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Labeled with 13N radionuclide

<400> SEQUENCE: 4

Cys Tyr Ile Gln Asn Cys Pro Leu Gly
1               5
```